US009617583B2

(12) United States Patent
Harley et al.

(10) Patent No.: US 9,617,583 B2
(45) Date of Patent: *Apr. 11, 2017

(54) METHOD FOR IDENTIFICATION OF SENSITIVITY OF A PATIENT TO TELOMERASE INHIBITION THERAPY

(71) Applicant: Geron Corporation, Menlo Park, CA (US)

(72) Inventors: Calvin B. Harley, Murphys, CA (US); Laurence Elias, Berkeley, CA (US); Jennifer Smith, Menlo Park, CA (US); Mark J. Ratain, Chicago, IL (US); Fabio Benedetti, San Francisco, CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/505,366

(22) Filed: Oct. 2, 2014

(65) Prior Publication Data

US 2015/0152488 A1    Jun. 4, 2015

Related U.S. Application Data

(62) Division of application No. 13/124,376, filed as application No. PCT/US2009/060526 on Oct. 13, 2009, now Pat. No. 8,877,723.

(60) Provisional application No. 61/106,491, filed on Oct. 17, 2008.

(51) Int. Cl.
*A61K 48/00* (2006.01)
*C07H 21/04* (2006.01)
*C12Q 1/68* (2006.01)

(52) U.S. Cl.
CPC ......... *C12Q 1/6813* (2013.01); *C12Q 1/6883* (2013.01); *C12Q 2600/106* (2013.01); *C12Q 2600/156* (2013.01)

(58) Field of Classification Search
CPC ............... A61K 48/00; A61K 2300/00; A61K 31/7088; C12N 2310/11
See application file for complete search history.

(56) References Cited

U.S. PATENT DOCUMENTS

| | | |
|---|---|---|
| 5,583,016 A | 12/1996 | Villeponteau et al. |
| 5,656,638 A | 8/1997 | Gaeta et al. |
| 5,686,245 A | 11/1997 | West |
| 5,695,932 A | 12/1997 | West et al. |
| 5,707,795 A | 1/1998 | West |
| 5,741,677 A | 4/1998 | Kozlowski et al. |
| 5,760,062 A | 6/1998 | Gaeta et al. |
| 5,767,278 A | 6/1998 | Gaeta et al. |
| 5,770,613 A | 6/1998 | Gaeta et al. |
| 5,776,679 A | 7/1998 | Villeponteau et al. |
| 5,834,193 A | 11/1998 | Kozlowski |
| 5,837,857 A | 11/1998 | Villeponteau et al. |
| 5,840,490 A | 11/1998 | Bacchetti et al. |
| 5,863,936 A | 1/1999 | Gaeta et al. |
| 6,261,836 B1 | 7/2001 | Cech et al. |
| 6,331,399 B1 | 12/2001 | Monia et al. |
| 6,368,789 B1 | 4/2002 | West et al. |
| 6,444,650 B1 | 9/2002 | Cech et al. |
| 6,514,693 B1 | 2/2003 | Lansdorp |
| 6,548,298 B2 | 4/2003 | Villeponteau et al. |
| 6,608,036 B1 | 8/2003 | Gryaznov et al. |
| 6,835,826 B2 | 12/2004 | Gryaznov et al. |
| 6,995,145 B1 | 2/2006 | Au et al. |
| 7,138,383 B2 | 11/2006 | Gryaznov et al. |
| 7,494,982 B2 | 2/2009 | Gryaznov et al. |
| 7,563,618 B2 | 7/2009 | Gryaznov et al. |
| 7,695,904 B2 | 4/2010 | Cawthon |
| 8,440,635 B2 | 5/2013 | Gryaznov et al. |
| 2004/0234961 A1 | 11/2004 | Fordyce et al. |
| 2005/0113325 A1 | 5/2005 | Gryaznov et al. |
| 2006/0009636 A1 | 1/2006 | Gryaznov et al. |
| 2006/0128651 A1 | 6/2006 | Au et al. |
| 2006/0210980 A1 | 9/2006 | Cawthon |
| 2007/0166753 A1 | 7/2007 | Mass et al. |
| 2008/0319054 A1* | 12/2008 | Kun .............. A61K 31/165 514/457 |
| 2010/0151477 A1 | 6/2010 | Cawthon |
| 2011/0195864 A1 | 8/2011 | Ma |
| 2011/0207128 A1 | 8/2011 | Cawthon et al. |
| 2014/0155465 A1 | 6/2014 | Bassett et al. |

FOREIGN PATENT DOCUMENTS

| | | |
|---|---|---|
| EP | 0870055 B1 | 5/2007 |
| WO | 98/28442 | 7/1998 |
| WO | 2005/023994 | 3/2005 |
| WO | 2007/067602 A1 | 6/2007 |
| WO | 2008/112129 | 9/2008 |

(Continued)

OTHER PUBLICATIONS

Dikmen et al. (Cancer Res 2005, 65, 17, 2005, pp. 7866-7873).*
Aviv, Abraham et al., "Impartial comparative analysis of measurement of leukocyte telomere length/DNA content by Southern blots and qPCR", Nucleic Acids Research, Aug. 8, 2011, 1-5.
Baerlocher, G. et al., "Flow cytometry and FISH to measure the average length of telomeres (flow FISH)", Nature Protocols 1(5), 2006, pp. 2365-2376.
Baerlocher, G. et al., "Telomere length measurement by fluorescence in situ hybridization and flow cytometry: tips and pitfalls", Cytometry 47, 2002, pp. 89-99.
Baerlocher, G. et al., "Telomere length measurement in leukocyte subsets by automated multicolor flow-FISH", Cytometry Part A 55A, 2003, pp. 1-6.
Baird, D. et al., "Extensive allelic variation and ultrashort telomeres in senescent human cells", Nature Genet. 33, 2003, pp. 203-207.

(Continued)

*Primary Examiner* — Amy Bowman
(74) *Attorney, Agent, or Firm* — Glenn J. Foulds; Carol L. Francis; Bozicevic, Field & Francis LLP

(57) ABSTRACT

The invention provides methods for determining the susceptibility of cancer patients to developing adverse reactions if treated with a telomerase inhibitor drug by measurement of telomere length in appropriate cells of the patient prior to initiation of the telomerase inhibitor treatment.

10 Claims, 7 Drawing Sheets

(56) References Cited

FOREIGN PATENT DOCUMENTS

| | | |
|---|---|---|
| WO | 2008/119027 A2 | 10/2008 |
| WO | 2009/073751 | 6/2009 |
| WO | 2014/085632 | 6/2014 |

OTHER PUBLICATIONS

Canela, A. et al., "High-throughput telomere length quantification by FISH and its application to human populations studies", Proc. Natl. Acad. Sci. USA 104(13), 2007, pp. 5300-5305.
Carpenter, R. et al., "Incidence and risk factors for side effects of spinal anesthesia", Anesthesiol. 76, 1992, pp. 905-916.
Cawthon, R. et al., "Association between telomere length in blood and mortality in people aged 60 years or older", The Lancet 361, 2003, pp. 393-395.
Cawthon, R., "Telomere length measurement by a novel monochrome multiplex quantitative PCR method", Nucl. Acids Res. 37(3), 2009, 7 pages.
Cawthon, Richard M., "Telomere measurement by quantitative PCR", Nucleic Acids Research, vol. 30, No. 10 e47, 2002, 1-6.
De Vivo, Immaculata et al., "A prospective study of relative telomere length and postmenopausal breast cancer risk", Cancer Epidemiol Biomarkers Prev. 18(4), 2009, 1152-1156.
Ehrlenbach, Silvia et al., "Influences on the reduction of relative telomere length over 10 years in the population-based Bruneck study", International J of Epidemiology 38, 2009, 1725.
Engelhardt, M. et al., "Telomerase activity and telomere length in pediatric patients with malignancies undergoing chemotherapy", Leukemia 12, 1998, pp. 13-24.
Flores, I. et al., "The longest telomeres: a general signature of adult stem cell compartments", Genes Dev. 22, 2008, pp. 654-667.
Harley, C. et al., "Telomerase and cancer therapeutics", Nat. Rev. Cancer 8(3), 2008, pp. 167-179.
Harley, C. et al., "Telomeres shorten during ageing of human fibroblasts", Nature 345, 1990, pp. 458-460.
Hochreiter, A. et al., "Telomerase template antagonist GRN163L disrupts telomere maintenance, tumor growth, and metastasis of breast cancer", Clin. Cancer Res. 12(10), 2006, pp. 3184-3192.
Kelland, Lloyd R., "Overcoming the immortality of tumour cells by telomere and telomerase based cancer therapeutics", Eur. J Cancer, 41, 2005, 971-979.
Kimura, M et al., "Leukocytes of exceptionally old persons display ultra-short telomeres", Am J Physiol Regul Integr Comp Physiol 293, 2007, R2210-R2217.
Lee, J.-J. et al., "Telomere length shortening in non-Hodgkin's lymphoma patients undergoing chemotherapy", Ann. Hematol. 82, 2003, pp. 492-495.
Ly, Hinh et al., "Functional characterization of telomerase RNA variants found in patients with hematologic disorders", Blood, vol. 105, No. 6, 2005, 2332-2339.
Meeker, Alan K. et al., "Telomere length abnormalities occur early in the initiation of epithelial carcinogenesis", Clinical Cancer Research vol. 10, May 15, 2004, 3317-3326.
Ratain, M. et al., "A phase I trial of GRN163L (GRN), a first-in-class telomere inhibitor, in advanced solid tumors", J. Clin. Oncol. 26, 2008, p. 3581.
Shayne, M. et al., "Dose intensity and hematologic toxicity in older cancer patients receiving systemic chemotherapy", Cancer 110(7), 2007, pp. 1611-1620.
Shen, Jing et al., "Short telomere length and breast cancer risk: a study in sister sets", Cancer Res. 67, 2007, 5538.
Shen, Jing et al., "Telomere length, oxidative damage, antioxidants and breast cancer risk", Int. J. Cancer 124, 2009, 1637.
Siegl-Cachedenier, Irene et al., "Telomerase reverses epidermal hair follicle stem cell defects and loss of long-term survival associated with critically short telomeres", J of Cell Biology, vol. 179, No. 2, Oct. 22, 2007, 277-290.
Svenson, Ulrika et al., "Breast cancer survival is associated with telomere length in peripheral blood cells", Cancer Res 68, 2008, 3618.
Svenson, Ulrika et al., "Telomere length in peripheral blood predicts survival in clear cell renal cell carcinoma", Cancer Res. 69, 2009, 2896.
Swarbrick, J. et al., "Dose Optimization in Drug Development", Taylor & Francis Group, LLC, New York, 2006, pp. 1-285.
Unryn, B. et al., "Acceleration of telomere loss by chemotherapy is greater in older patients with locally advanced head and neck cancer", Clin. Cancer Res. 12(21), 2006, pp. 6345-6350.
Van Ziffle, Jessica A. et al., "Telomere length in subpopulations of human hematopoetic cells", Stem Cells 21, 2003, 654-660.
Xu, Lifeng et al., "Human cancer cells harbor T-stumps, a distinct class of extremely short telomeres", Mol Cell 28 (2), 2007, 315-327.
Yoon, S. Y. et al., "Telomere length shortening of peripheral blood mononuclear cells in solid-cancer patients undergoing standard-dose chemotherapy might be correlated with good treatment response and neutropenia severity", Acta Haematol. 118, 2007, pp. 30-37.
PCT Search Report for PCT/US2009/060526, dated Dec. 9, 2009, 2 pages.
Supplemental European Search Report for EP 09821131.1, dated Aug. 23, 2012.
Allsopp, et al., Proc. Natl. Acad. Sci USA, vol. 89, 1992, 10114-10118.
Asai, A. et al., "A Novel Telomerase Template Antagonist (GRN163) as a Potential Anticancer Agent", Cancer Res. 63, 2003, pp. 3931-3939.
Baerlocher, et al., Methods in Cell Biol. 75, 2004, 719-750.
Blackburn, E., "Structure and function of telomeres", Nature 350, 1991, 569-73.
Chen, J. et al., "Secondary structure of vertebrate telomerase RNA", Cell 100, 2000, pp. 503-514.
De Lange, T. et al., "Structure and variability of human chromosome ends", Mol. Cell. Biol. 10(2), (1990), pp. 518-527.
Dikmen, Z. et al., "In vivo inhibition of lung cancer by GRN163L: A novel human telomerase inhibitor", Cancer Res. 65, (2005), pp. 7866-7873.
Djojosobruto, MW et al., Hepatol 42, 2005, 1-11.
Gowan, S. et al., "A G-quadruplex-interactive potent small-molecule inhibitor of telomerase exhibiting in vitro and in vivo anti-tumor activity", Mol. Pharmacol. 61(5), (2002), pp. 1154-1162.
Greider, C. et al., "A telomeric sequence in the RNA of Tetrahymena telomerase required for telomere repeat synthesis", Nature 337, 1989, 331-7.
Greider, C. et al., "Identification of a specific telomere terminal transferase activity in Tetrahymena extracts", Cell 43, 1985, pp. 405-413.
Greider, C. et al., "Telomeres, telomerase and cancer", Sci. Am. 274(2), 1996, pp. 92-97.
Gryaznov, S. et al., "Oligonucleotide N3'->P5' thiophosphoramidate telomerase template antagonists as potential anticancer agents", Nucleosides, Nucleotides & Nucl. Acids 22(5-8), (2003), pp. 577-581.
Hastie, N. et al., "Telomere reduction in human colorectal carcinoma and with ageing", Nature 346, 1990, pp. 866-868.
Kim, M. et al., "A low threshold level of expression of mutant-template telomerase RNA inhibits human tumor cell proliferation", Proc. Natl. Acad. Sci. USA 98(14), 2001, pp. 7982-7987.
Kim, N. et al., "Specific association of human telomerase activity with immortal cells and cancer", Science 266, 1994, pp. 2011-2015.
Kupihar, Z. et al., "Synthesis and application of a novel, crystalline phosphoramidite monomer with thiol terminus, suitable for the synthesis of DNA conjugates", Bioorg. Med. Chem. 9(5), (2001), pp. 1241-1247.
Lebedeva, I. et al., "Antisense oligonucleotides: promise and reality", Annu. Rev. Pharmacol. Toxicol. 41, (2001), pp. 403-419.
Macejak, D. et al., "Adenovirus-mediated expression of a ribozyme to c-myb mRNA inhibits smooth muscle cell proliferation and neointima formation in vivo", J. Virol. 73(9), (1999), pp. 7745-7751.
McClintock, "The Stability of Broken Ends of Chromosomes in Zea mays", Genetics vol. 26 (2), 1941, 234-282.

(56) References Cited

OTHER PUBLICATIONS

McCurdy, S. et al., "An Improved Method for the Synthesis of N3'->P5' Phosphoramidate Oligonucleotides", Tetrahedron Lett. 38(2), (1997), pp. 207-210.

Mishra, R. et al., "Improved leishmanicidal effect of phosphorotioate antisense oligonucleotides by LDL-mediated delivery", Biochim. Biophys. Acta 1264(2), 1995, pp. 229-237.

Morin, G. et al., "The human telomere terminal transferase enzyme is a ribonucleoprotein that synthesizes TTAGGG repeats", Cell 59, 1989, pp. 521-529.

Muller, HJ , "The remaking of chromosomes", The Collecting Net-Woods Hole vol. 13, 1938, 181-198.

Nelson, J. et al., "N3'-P5' oligodeoxyribonucleotide phosphoramidates: a new method of synthesis based on a phosphoramidate amine-exchange reaction", J. Org. Chem. 62, 1997, pp. 7278-7287.

Pascolo, E. et al., "Mechanism of human telomerase inhibition by BIBR1532, a synthetic, non-nucleosidic drug candidate", J. Biol. Chem. 277(18), (2002), pp. 15566-15572.

Pongracz, K. et al., "Oligonucleotide N3'→P5' thiophosphoramidates: synthesis and properties", Tetrahedron Lett. 49, (1999), pp. 7661-7664.

Pruzan, R. et al., "Allosteric inhibitors of telomerase: oligonucleotide N3'→>P5' phosporamidates", Nucl. Acids Res. 30(2), 2002, pp. 559-568.

Rump, E. et al., "Preparation of conjugates of oligodeoxynucleotides and lipid structures and their interaction with low-density lipoprotein", Bioconjugate Chem. 9, (1998), pp. 341-349.

Shay, J.W. et al., "Senescence and Immortalization: Role of Telomeres and Telomerase", Carcinogenesis 26(5), 2005, 867-874.

Shea, R. et al., "Synthesis, hybridization properties and antiviral activity of lipid-oligodeoxynucleotide conjugates", Nucl. Acids Res. 18(13), 1990, pp. 3777-3783.

Shea-Herbert, B. et al., "Lipid modification of GRN163, an N3'-P5' thio-phosphoramidate oligonucleotide, enhance the potency of telomerase inhibition", Oncogene 24, 2005, pp. 5262-5268.

Shea-Herbert, B. et al., "Oligonucleotide N3'→P5' phosphoramidates as efficient telomerase inhibitors", Oncogene 21, 2002, pp. 638-642.

Uhlmann, E. et al., "Antisense oligonucleotides: a new therapeutic principle", Chem. Rev. 90, (1990), pp. 543-584.

Vaziri, et al., "Loss of Telomeric DNA during Aging of Normal and Trisomy 21 Human Lymphocytes", Amer. J. Hum. Genet., vol. 52, 1993, 661-667.

Ward, R. et al., "Pharmacological telomerase inhibition can sensitize drug-resistant and drug-sensitive cells to chemotherapeutic treatment", Mol. Pharmacol. 68, (2005), pp. 779-786.

Zeng, Y. et al., "MicroRNAs and small interfering RNAs can inhibit mRNA expression by similar mechanisms", Proc. Natl. Acad. Sci. USA 100(17), (2003), pp. 9779-9784.

\* cited by examiner

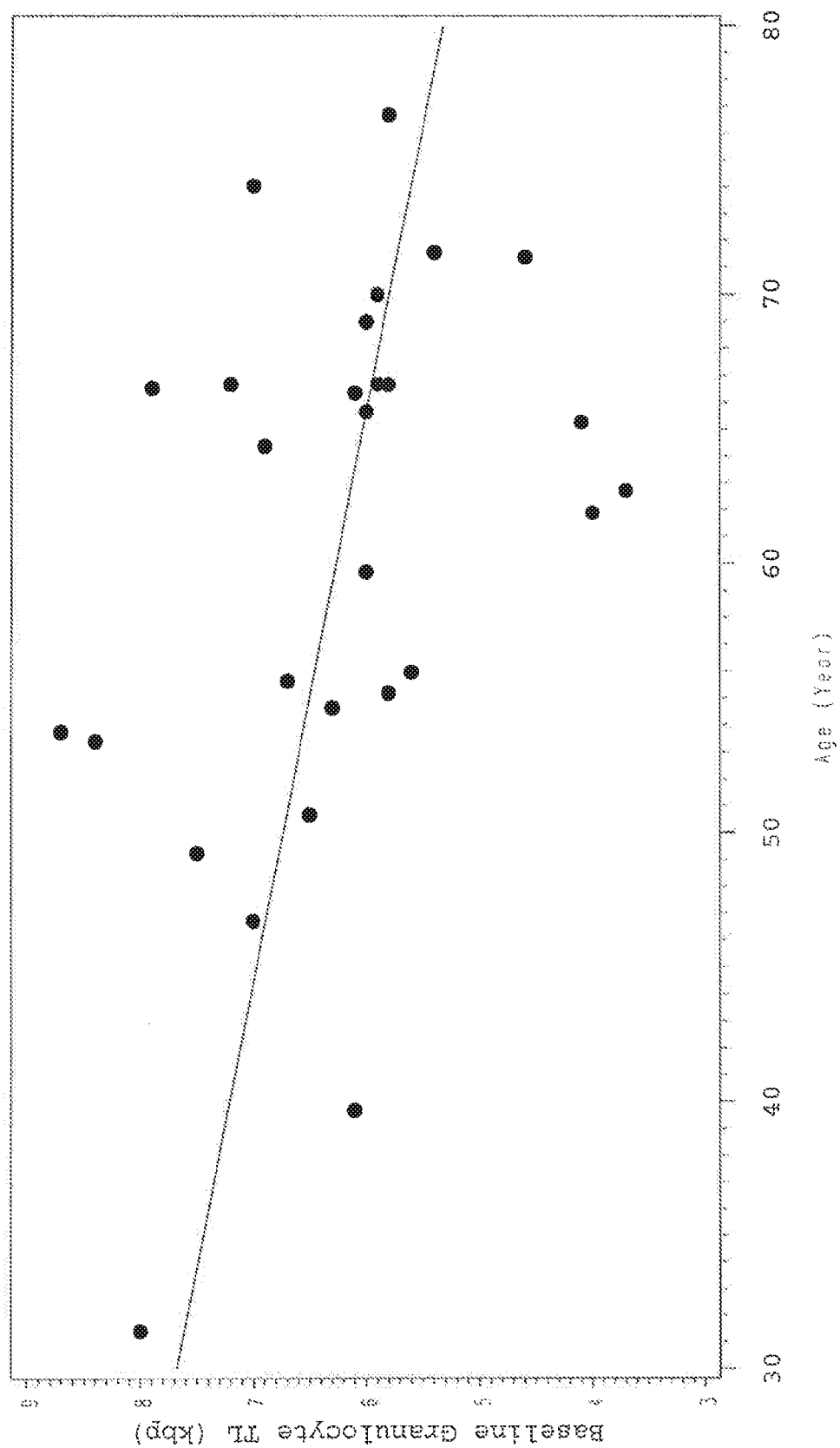

SEQUENCE LISTING

```
<160> NUMBER OF SEQ ID NOS: 3

<210> SEQ ID NO 1
<211> LENGTH: 11
<212> TYPE: RNA
<213> ORGANISM: Homo sapiens

<400> SEQUENCE: 1
cuaacccuaa c                                                            11

<210> SEQ ID NO 2
<211> LENGTH: 13
<212> TYPE: DNA
<213> ORGANISM: Artificial sequence
<220> FEATURE:
<223> OTHER INFORMATION: GRN-163

<400> SEQUENCE: 2
tagggttaga caa                                                          13

<210> SEQ ID NO 3
<211> LENGTH: 18
<212> TYPE: DNA
<213> ORGANISM: Artificial Sequence
<220> FEATURE:
<223> OTHER INFORMATION: PNA probe

<400> SEQUENCE: 3
ccctaaccct aaccctaa                                                     18
```

METHOD FOR IDENTIFICATION OF SENSITIVITY OF A PATIENT TO TELOMERASE INHIBITION THERAPY

REFERENCE TO RELATED APPLICATIONS

This application is a continuation of U.S. Ser. No. 13/124,376, filed Apr. 14, 2011, which is a 371 of PCT Application Serial No. PCT/US09/60526, filed Oct. 13, 2009, which claims priority to U.S. Ser. No. 61/106,491, filed Oct. 17, 2008, which applications are hereby incorporated herein by reference in their entirety.

FIELD OF THE INVENTION

The invention relates generally to the field of identification of patients who are sensitive to telomerase inhibiting agents. In particular the invention provides methods for detecting patients who should limit or modify the use of telomerase inhibitors because they are in a risk category for developing limiting sensitivity such as thrombocytopenia.

BACKGROUND

Telomeres are genetic elements located at the ends of all eukaryotic chromosomes which preserve genome stability and cell viability by preventing aberrant recombination and degradation of DNA (McClintock, 1941, *Genetics* vol 26, (2) pp 234-282; Muller, (1938) *The collecting net*, vol 13, (8) pp 181-198). In humans, the telomeric sequence is composed of 10-20 kilobases of TTAGGG repeats (Harley et al., 1990) *Nature* vol. 345 pp 458-460; Blackburn, (1991) *Nature* vol. 350 pp 569-573; de Lange et al., (1990) *Mol. Cell Biol*. Vol 10, (2) pp 518-527). There is increasing evidence that gradual loss of telomeric repeat sequences (TTAGGG) may be a timing ("clock") mechanism limiting the number of cellular divisions in normal human cells (Allsopp et al., (1992) *Proc. Natl. Acad. Sci.* USA, vol. 89, pp. 10114-10118; Harley et al., (1990) *Nature*, vol. 345, pp. 458-460; Hastie et al., (1990) *Nature*, vol. 346, pp. 866-868; Vaziri et al., (1993) *Amer. J. Hum. Genet.*, vol. 52, pp. 661-667). In contrast, immortal cells are capable of maintaining a stable telomere length by upregulating or reactivating telomerase, a ribonucleoprotein enzyme that is able to add telomeric repeats to the ends of chromosomes (Greider and Blackburn, (1985) *Cell*, vol. 43, pp. 405-413; Greider and Blackburn, (1989) *Nature*, vol. 337, pp. 331-337; Morin, (1989) *Cell*, vol. 59, pp. 521-529).

Telomerase is an enzyme which adds nucleotides to the telomeres at the ends of chromosomes, helping to prevent telomeric shortening to critical lengths. Structurally telomerase is a unique macromolecular complex which incorporates a strand of RNA in its active site. This RNA includes telomeric complementary sequence (3'-AUCCCAAUC-5'), which functions both to anchor telomerase to the telomere and as a template for adding repeats to the chromosome end. Telomerase is active in essentially all cancers, but is generally present at very low or non-detectable levels in normal adult tissue. Thus, the average telomere length of normal cells varies among individuals and declines with age (see FIG. 7). Telomere shortening in normal tissues may also be accelerated by oxidative, physiologic or immunologic stress and exposure to toxic agents.

Cancer cells generally undergo repeated rounds of cell division and have telomeres that are stable, but shorter than those in normal cells. Telomerase activation is necessary for most cancer cells to replicate indefinitely and thereby enables tumor growth and metastasis. (Kim et al., *Science* vol. 266 pp 2011-2015; Greider C W, Blackburn E H. *Sci Am* February: 92-97, 1996; Shay J W and Wright W E. "Senescence and immortalization: role of telomeres and telomerase" *Carcinogenesis* 26:867-74, 2005). Therefore inhibition of telomerase is considered a promising treatment strategy for a broad variety of solid tumor types and hematological malignancies (Harley C B, *Nature Rev. Cancer*, vol. 8 pp 167-179, 2008).

GRN163L is a thio-phosphoramidate oligonucleotide with a 5' palmitoyl "tail". It inhibits the activity of intracellular telomerase by binding to the template region of the RNA component of the telomerase holoezyme. (Shea-Herbert et al *Oncogene* 24:5262-8, 2005) GRN163L has demonstrated telomerase inhibition and cancer cell growth inhibition effects both in vitro and in vivo (Dikmen Z G, et al. *Cancer Res*. 65:7866-73, 2005; Djojosobruto M W et al. *Hepatol* 42:1-11, 2005; Hochreiter A E, et al. *Clin Cancer Res* 12:3184-92 2006) GRN163L is currently in clinical trials in solid tumor and hematological cancers.

In any cancer treatment, chemotherapy-induced toxicity can result in reductions in relative dose intensity of the chemotherapy. Treatment-induced toxicities can include anemia, neutropenia, leucopenia and thrombocytopenia. Thrombocytopenia is a chemotherapy-induced toxicity that typically occurs in the first round of chemotherapy treatment and may become more severe during repeated rounds of treatment. Drugs that result in toxicities may have limited applications because of reduced dose intensity (RDI), dose delays and relative dose reductions. Such dose reductions, reduced dose intensity or dose delays used as a means of reducing toxicity may undermine disease control and overall survival, particularly in patients with potentially curable malignancies. It is generally recommended that in order to gain maximum benefit-risk ratio from chemotherapy, the dose prescribed should be individualized according to the goal of therapy and response.

Treatment of thrombocytopenia is determined by the etiology and disease severity. The main concept in treating thrombocytopenia is to eliminate the underlying problem, whether that means discontinuing suspected drugs that cause thrombocytopenia, or treating contributing immunologic or inflammatory factors. Patients with severe thrombocytopenia may be managed with transfusions of donor platelets for a period of time. In addition, Oprelvekin (NEUMEGA™, Wyeth) is approved for the prevention of severe thrombocytopenia following myelosuppresive chemotherapy in adult patients with nonmyeloid malignancies. Another drug, Romiplostin (NPLATE™, Amgen Inc.) has been approved for the treatment of chronic idiopathic thrombocytopenic purpura (ITP).

In this context, a highly predictive test for patients who are sensitive to developing telomerase inhibition therapy-induced toxicity would provide significant reduction in the total burden of toxicity associated with telomerase inhibition therapy, and allow for the safer use of telomerase inhibition therapy without inappropriate denial of access to its use.

The present invention seeks to present a method for determining the susceptibility of cancer patients to developing treatment limiting toxicities, such as thrombocytopenia, from telomerase inhibition therapy.

SUMMARY OF THE INVENTION

The invention provides methods of determining the susceptibility of cancer patients to develop toxicities if treated with a telomerase inhibitor drug. The invention requires the measurement of telomere lengths in appropriate cells of the patient prior to initiation of the telomerase inhibitor treatment and the correlation of the telomere length measurement with susceptibility to thrombocytopenia. In one embodiment, an algorithm is provided to assist with the correlation.

The invention provides a method of monitoring a patient for an adverse event related to telomerase inhibition therapy wherein the method comprises testing a biological sample from the patient for the length or length distribution of telomeres. The method may further comprise the step of identifying the likelihood that a mammalian subject will exhibit an adverse reaction to treatment with a telomerase inhibition therapy.

The invention includes a method for identifying the likelihood that a mammalian subject will exhibit an adverse reaction to telomerase inhibition therapy comprising,
(a) determining the average or median telomere length in a biological sample comprising cells obtained from the mammalian subject prior to or at the time of treatment with a telomerase inhibition therapy and multiplying the average or median telomere length by a coefficient to arrive at a telomere length component;
(b) multiplying the intended treatment dosage by a coefficient to arrive at a dosage component;
(c) calculating the sum of the telomere component, the dosage component and a constant; and
(d) determining the expected likelihood of an adverse reaction in the mammalian subject from treatment with the telomerase inhibition therapy.

In one aspect of the method, the mammalian subject is a human.

In one aspect of the method, the adverse reaction is selected from thrombocytopenia, anemia, leucopenia, or neutropenia.

The method wherein the adverse reaction is thrombocytopenia and the sum of the telomere component, the dosage component and the constant determines the percentage decrease of the mammalian subject's platelet number from the subject's baseline platelet number prior to treatment. The method wherein the adverse reaction is any grade of thrombocytopenia. The method wherein the adverse reaction is grades 3 or 4 thrombocytopenia.

In an aspect of the method, the biological sample is blood cells obtained from the mammalian subject. In one aspect the blood cells are white blood cells. The method wherein the white blood cells are selected from granulocytes or lymphocytes. In one aspect the blood cells are granulocytes. The granulocytes are selected from neutrophils, basophils or eosinophils. In another aspect the blood cells are lymphocytes. In another aspect the blood cells are monocytes or macrophages.

In an aspect of the method, the mammalian subject is being treated with the telomerase inhibitor to treat cancer. In an aspect of the method, the telomerase inhibitor is an oligonucleotide. In an aspect of the method, the telomerase inhibitor is GRN163L.

In an aspect of the method, the cancer is selected from the group consisting of breast cancer, colon cancer, lung cancer, prostate cancer, testicular cancer, gastric cancer, gastrointestinal cancer, pharynx cancer, rectal cancer, pancreatic cancer, cervical cancer, ovarian cancer, liver cancer, bladder cancer, cancer of the urinary tract, thyroid cancer, renal cancer, skin cancer, brain cancer, leukemia, myeloma and lymphoma.

In an aspect of the method, the telomere length component is a positive component when calculating the percentage change.

In an aspect of the method, the dosage component is a negative component when calculating the percentage change.

In an aspect of the method, the method further comprises the step of assigning to the subject the likelihood of having an adverse reaction to telomerase inhibitor treatment.

In an aspect of the method, the shorter baseline telomere lengths are associated with an increased risk of an adverse reaction.

In an aspect of the method, the increased dosage is associated with an increased risk of an adverse reaction.

In an aspect of the method, the baseline telomere length is determined by FISH analysis, Southern blot analysis, PCR analysis or STELA analysis.

In an aspect of the method, the baseline telomere length is determined by FISH analysis.

According to another aspect of the present invention there is provided a method of determining the likelihood that a mammalian subject will experience thrombocytopenia related to telomerase inhibition therapy wherein the method comprises,
(a) determining the average or median telomere length in a biological sample comprising cells obtained from the mammalian subject prior to or at the time of treatment with a telomerase inhibition therapy and multiplying the average or median telomere length by a coefficient to arrive at a telomere length component;
(b) multiplying the intended treatment dosage by a coefficient to arrive at a dosage component;
(c) calculating the sum of the telomere component and the dosage component and the log of the subject's baseline platelet number to determine the predicted platelet nadir during the first weeks of treatment; and
(d) determining the expected likelihood of thrombocytopenia in the mammalian subject from treatment with the telomerase inhibition therapy.

According to another aspect of the present invention there is provided a method to identify a patient potentially requiring a telomerase inhibitor dose level below the maximum recommended dose level, in which the method comprises
(a) determining the average or median telomere length in a biological sample comprising cells obtained from the mammalian subject prior to or at the time of treatment with a telomerase inhibition therapy and multiplying the average or median telomere length by a coefficient to arrive at a telomere length component;
(b) multiplying the intended treatment dosage by a coefficient to arrive at a dosage component;
(c) calculating the sum of the telomere component and the dosage component and the log of the subject's baseline platelet number to determine the predicted platelet nadir during the first weeks of treatment;
(d) determining the expected likelihood of thrombocytopenia in the mammalian subject from treatment with the telomerase inhibition therapy; and
(e) administering a reduced dose of the telomerase inhibitor or a reduced dosage regimen of the telomerase inhibitor.

According to another aspect of the present invention there is provided a method to identify a mammalian subject requiring an ameliorating pharmaceutical administered in conjunction with a telomerase inhibitor in which the method comprises
(a) determining the average or median telomere length in a biological sample comprising cells obtained from the mammalian subject prior to or at the time of treatment with a telomerase inhibition therapy and multiplying the average or median telomere length by a coefficient to arrive at a telomere length component;

(b) multiplying the intended treatment dosage by a coefficient to arrive at a dosage component; and (c) calculating the sum of the telomere component and the dosage component and the log of the subject's baseline platelet number to determine the predicted platelet nadir during the first weeks of treatment; and (d) determining the expected likelihood of thrombocytopenia in the mammalian subject from treatment with the telomerase inhibition therapy (e) administering an appropriate dosage of an ameliorating pharmaceutical in conjunction with the telomerase inhibitor.

According to another aspect of the invention there is provided a method for identifying a mammalian subject on telomerase inhibition therapy that requires adverse event monitoring comprising testing a non-cancerous biological sample from the mammalian subject for telomere length prior to telomerase inhibition therapy.

Preferably the method further comprises monitoring the mammalian subject for an adverse reaction relating to treatment with the telomerase inhibitor.

According to another aspect of the invention there is provided a computer-accessible medium comprising a database that includes a plurality of records, wherein each record associates (a) information that identifies a mammalian subject, with (b) information that indicates whether the subject has shortened telomeres and wherein each record further associates (a) with (c) information that identifies the presence or absence of an adverse event in the subject resulting from administration of a telomerase inhibitor to the subject.

According to another aspect of the invention there is provided a method for administration of GRN163L which comprises administration of about 1.6 mg/kg to about 20 mg/kg of GRN163L on day 1 and on approximately day 8 of a 21 day cycle.

According to another aspect of the invention there is provided a method for administration of GRN163L which comprises administration of about 1.6 mg/kg to about 20 mg/kg of GRN163L on day 1 and on approximately day 15 of a 28 day cycle.

According to another aspect of the invention there is provided a method for administration of GRN163L which comprises administration of about 1.6 mg/kg to about 20 mg/kg of GRN163L two times in the first week in a 14 day cycle.

Other aspects and advantages of the invention will become more fully apparent when the following detailed description of the invention is read in conjunction with the accompanying drawings.

BRIEF DESCRIPTION OF THE DRAWINGS

FIG. 7 is a graph showing the change in telomere length as a function of age.

DETAILED DESCRIPTION OF THE INVENTION

Figure 1:
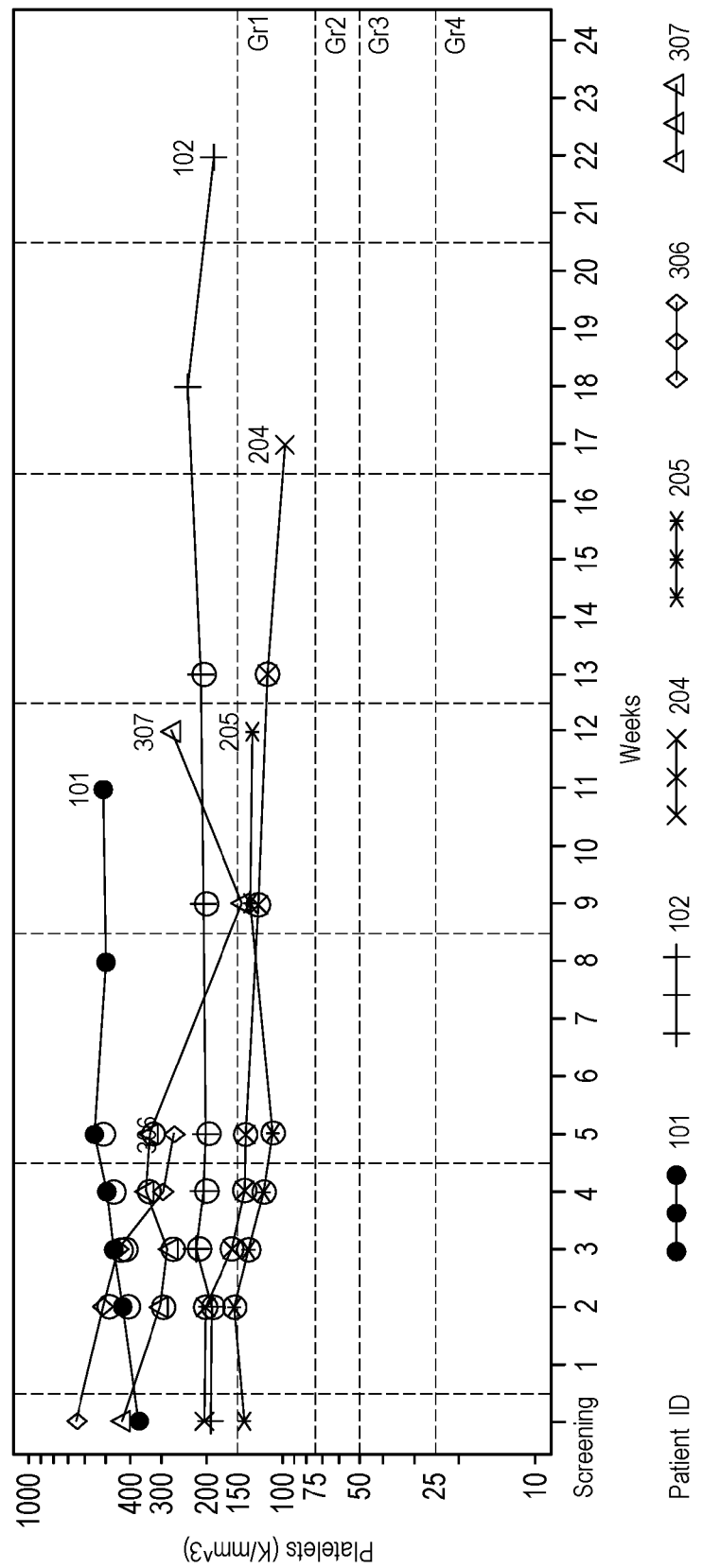
FIG. 1 is a graph showing platelet levels over time for individual patients in cohorts 1-3 of the study. Broken horizontal lines show the ranges for different levels of thrombocytopenia. Circles at time points indicate that the patients received a dose of GRN163L and platelets were collected.

Those skilled in the art will appreciate that the invention described herein is susceptible to variations and modifications other than those specifically described, including the addition of other risk factor components which may be relevant to different patient populations or combinations of telomerase inhibition therapy with other treatments. It is to be understood that the invention includes all such variations and modifications. The invention also includes all of the steps, features, compositions and compounds referred to or indicated in the specification, individually or collectively, and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

All references cited, including patents or patent applications are hereby incorporated by reference. No admission is made that any of the references constitute prior art.

A. Definitions

The terms below have the following meanings unless indicated otherwise.

A "mammalian subject", "subject" or "patient" refers to a mammal. For the purposes of this invention, mammals include humans; agriculturally important mammals, such as cattle, horses, sheep; and/or veterinary mammals, such as cats, rabbits, rodents and dogs. A "patient" means a subject who is receiving medical or veterinary treatment.

A "dose" means quantity to be administered at one time, such as a specified amount of medication. For GRN163L, the adult starting dose is from about 0.8 mg/kg to about 50 mg/kg; from about 1.6 mg/kg to about 20 mg/kg. The adult dose for GRN163L is from about 1.6 mg/kg; or about 3.2 mg/kg; or about 4.8 mg/kg; or about 6.2 mg/kg; or about 7.2 mg/kg; or about 9 mg/kg; or about 12 mg/kg; to about 20 mg/kg. The dose may be administered twice weekly, once weekly or at other rates of administration. Higher doses may be required to produce the desired remission in some patients. The doses may be administered by a 2-24 hour infusion, more preferably by a 2-4 hour infusion.

The term "baseline telomere length" or "average or median baseline telomere length" means the average or median length of the patient's telomeres in the appropriate cells prior to or at the same time that the patient receives the first treatment of the telomerase inhibitor.

The term "platelet nadir during the first weeks of treatment" means the number of platelets present in the patient or subjects blood at the lowest point in the first weeks after treatment. The first weeks of treatment means in weeks 1-12 of treatment, preferably 1-8 of treatment, preferable 1-6 of treatment, preferably 1-4 of treatment.

"Adverse event" or "adverse reaction" means the development of an undesirable medical condition or the deterioration of a pre-existing medical condition following or during exposure to a pharmaceutical product. An adverse reaction can be selected from thrombocytopenia, anemia, leucopenia, or neutropenia. Where the adverse reaction is thrombocytopenia and the sum of the telomere component and the dosage component and a constant determines the percentage decrease of the mammalian subject's platelet count from the subjects platelet count prior to treatment. Where the adverse reaction is thrombocytopenia, the adverse reaction may be any grade of thrombocytopenia. The adverse reaction may be grades 3 or 4 thrombocytopenia.

Thrombocytopenia has been classified into different grades depending on the number of platelets in the mammalian subject's blood.

| Grade of Thrombocytopenia | Number of platelets/microliter |
| --- | --- |
| Grade 1 | 75-150,000 |
| Grade 2 | 50-75,000 |
| Grade 3 | 25-50,000 |
| Grade 4 | <25,000 |

The term "neutropenia" means the presence of abnormally small numbers of neutrophils in the blood.

The term "leucopenia" means an abnormally low number of white blood cells in the blood.

The term "anemia" means a deficiency in the oxygen-carrying component of the blood, measured in unit volume concentrations of hemoglobin, red blood cell volume or red blood cell number.

The term "number of baseline platelets" means the number of platelets per microliter of the mammalian subject's blood prior to treatment with the telomerase inhibitor.

"Benefit risk ratio" means the relation between the risks and benefits of a given treatment or procedure. An acceptable risk relates to the potential for suffering disease or injury that will be tolerated by an individual in exchange for the benefits of using a substance or process that will cause such disease or injury. Acceptability of risk depends on scientific data, social and economic factors, and on the perceived benefits arising from a chemical or drug that creates the risk(s) in question.

A "biological sample" is a blood sample or tissue sample from the mammalian subject. In one aspect the biological sample is blood containing white blood cells. In one aspect the white blood cells are granulocytes. Granulocytes are one or more of neutrophils, basophils or eosinophils. In another aspect the white blood cells are one or more of lymphocytes, monocytes or macrophages. Preferably the cells are non-cancerous or normal cells.

A "telomerase inhibitor" is a compound that directly or indirectly inhibits or blocks the expression or activity of telomerase. A telomerase inhibitor is said to inhibit or block telomerase if the activity of the telomerase in the presence of the compound is less than that observed in the absence of the compound. Preferably the telomerase is human telomerase. Preferably the telomerase inhibitor is an active site inhibitor. More preferably, the telomerase inhibitor is an hTR template antagonist.

A "polynucleotide" or "oligonucleotide" refers to a ribose and/or deoxyribose nucleoside subunit polymer or oligomer having from about 2 to about 200 contiguous subunits, from about 5 to about 20 contiguous subunits, from about 10 to about 15 subunits. The nucleoside subunits can be joined by a variety of intersubunit linkages, including, but not limited to, phosphodiester, phosphotriester, methylphosphonate, P3'→N5' phosphoramidate, N3'→P5' phosphoramidate, N3'4→P5' thiophosphoramidate, and phosphorothioate linkages. The term also includes such polymers or oligomers having modifications, known to one skilled in the art, to the sugar (e.g., 2' substitutions), the base (see the definition of "nucleoside" below), and the 3' and 5' termini. In embodiments where the oligonucleotide moiety includes a plurality of intersubunit linkages, each linkage may be formed using the same chemistry, or a mixture of linkage chemistries may be used. When an oligonucleotide is represented by a sequence of letters, such as "ATGUCCTG," it will be understood that the nucleotides are in 5'→3' order from left to right. Representation of the base sequence of the oligonucleotide in this manner does not imply the use of any particular type of internucleoside subunit or modifications in the base component or elsewhere in the oligonucleotide.

The term "nucleoside" includes the natural nucleosides, including 2'-deoxy and 2'-hydroxyl forms, e.g., as described in Komberg and Baker, DNA Replication, 2nd Ed. (Freeman, San Francisco, 1992), and analogs. "Analogs", in reference to nucleosides, includes synthetic nucleosides having modified nucleobase moieties (see definition of "nucleobase" below) and/or modified sugar moieties, e.g., described generally by Scheit, *Nucleotide Analogs* (John Wiley, New York, 1980). Such analogs include synthetic nucleosides designed to enhance binding properties, e.g., stability, specificity, or the like, such as disclosed by Uhlmann and Peyman (*Chemical Reviews* 90:543-584, 1990). An oligonucleotide containing such nucleosides, and which typically contains synthetic nuclease-resistant internucleoside linkages, may itself be referred to as an "analog".

A "nucleobase" includes (i) native DNA and RNA nucleobases (uracil, thymine, adenine, guanine, and cytosine), (ii) modified nucleobases or nucleobase analogs (e.g., 5-methylcytosine, 5-bromouracil, or inosine) and (iii) nucleobase analogs. A nucleobase analog is a compound whose molecular structure mimics that of a typical DNA or RNA base.

An oligonucleotide having "nuclease-resistant linkages" refers to one whose backbone has subunit linkages that are substantially resistant to nuclease cleavage, in non-hybridized or hybridized form, by common extracellular and intracellular nucleases in the body; that is, the oligonucleotide shows little or no nuclease cleavage under normal nuclease conditions in the body to which the oligonucleotide is exposed. The N3'→P5' phosphoramidate (NP) or N3'→P5' thiophosphoramidate (NPS) linkages described below are nuclease resistant.

The term "lipid" is used broadly herein to encompass substances that are soluble in organic solvents, but sparingly soluble, if at all, in water. The term lipid includes, but is not limited to, hydrocarbons, oils, fats (such as fatty acids and glycerides), sterols, steroids and derivative forms of these compounds. Preferred lipids are fatty acids and their derivatives, hydrocarbons and their derivatives, and sterols, such as cholesterol.

Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty or esters.

The term "hydrocarbon" encompasses compounds that consist only of hydrogen and carbon, joined by covalent bonds. The term encompasses open chain (aliphatic) hydrocarbons, including straight chain and branched hydrocarbons, and saturated as well as mono- and poly-unsaturated hydrocarbons. The term also encompasses hydrocarbons containing one or more aromatic rings.

As used herein, the term "lipid" also includes amphipathic compounds containing both lipid and hydrophilic moieties.

The term "tumor" as used herein, refers to all neoplastic cell growth and proliferation, whether malignant or benign, and all pre-cancerous and cancerous cells and tissues.

An "ameliorating pharmaceutical" is a pharmaceutical which can lessen or remove the risk of developing the adverse reaction. For example, Oprelvekin (NEUMEGA™, Wyeth) is approved for the prevention of severe thrombocytopenia following myelosuppresive chemotherapy in adult patients with nonmyeloid malignancies. Another drug, Romiplostin (NPLATE™, Amgen Inc.) has been approved for the treatment of chronic idiopathic thrombocytopenic purpura (ITP).

A "cancer" may be a malignant tumor. At least 80% of all cancers are carcinomas, and include but are not limited to breast cancer, both ductal and lobular carcinomas of the breast; colon cancer, lung cancer, prostate cancer, testicular cancer, gastric cancer, gastrointestinal cancer, pharynx cancer, rectal cancer, pancreatic cancer, cervical cancer, ovarian cancer; liver cancer (including hepatocellular carcinoma), bladder cancer, cancer of the urinary tract, thyroid cancer, renal cancer, skin cancer (including basal-cell carcinoma, the most common non-melanoma skin cancer and squamous cell carcinoma, a common form of skin cancer), and brain cancer. The cancer cells making up a carcinoma are referred to as "carcinoma cells." Also included in the term "cancer" are cancers of the blood cells such as leukemias, lymphomas and myelomas and cancers of other types of tissue such as sarcomas, mesothelioma, gliomas, melanoma, neuroblatoma, etc.

A "prognosis" is used herein to refer to the prediction of the likelihood of an adverse reaction to treatment with a telomerase inhibitor. The term "prediction" is used herein to refer to the likelihood that a mammalian subject or patient will respond either favorably or unfavorably to a drug or a set of drugs, and also the extent of those responses.

In term "adjuvant therapy" is generally used to refer to treatment that is given in addition to a primary (initial) treatment. In cancer treatment, the term "adjuvant therapy" is used to refer to chemotherapy, hormonal therapy and/or radiation therapy following surgical removal of the tumor, with the primary goal of reducing the risk of cancer recurrence.

B. Detailed Description

The practice of the present invention will employ, unless otherwise indicated convention techniques of molecular biology, microbiology, cell biology and biochemistry which are within the skill of the art. Such techniques are explained fully in the literature, such as "Molecular Cloning: A Laboratory Manual", $2^{nd}$ edition (Sambrook et al., 1989); Oligonucleotide Synthesis: A practical Approach (M. J. Gait ed, 1984); "Current Protocols in Molecular Biology" (F. M. Ausubel et al., eds. 1987) and "PCR: The Polymerase Chain reaction" (Mullis et al., eds. 1994).

The present invention provides an algorithm for determining the likelihood of an adverse reaction to treatment with a telomerase inhibitor. The method is based on the identification of (1) the average or median telomere length in a cells from a patient and the dosage of telomerase inhibitor received can serve to determine the likelihood of the patient suffering an adverse reaction to therapy with the telomerase inhibitor, (2) certain weights assigned to the average or median telomere length and the dosage reflect their value in predicting the response to therapy and used in a formula; and (3) determination of threshold values used to divide patients into groups with varying degrees of risk to developing an adverse reaction, such as low, medium and high risk groups or groups in which the likelihood of an adverse reaction to telomerase inhibitors is low, medium or high. The algorithm yields a numerical score which can be used to make treatment decisions concerning the therapy of cancer patients.

1. Techniques for Determination of Telomere Length.

Several methods are available for measuring the length of telomere repeats in cells. Generally the cells whose telomeres are to be measured are isolated from the biological sample of the patient. The DNA is isolated from the cells by methods known in the art, such as for example, proteinase K, RNAse A and phenol/chloroform protocols (Sambrook et al. *Molecular Cloning: a Laboratory Manual* 2nd ed. (1989) or use of commercially available DNA purification kits.

A. Southern Blot Analysis

One method for the analysis of telomere lengths is to measure the length of the terminal restriction fragment (TRF) by Southern Blot analysis. In this method cellular DNA is digested with the restriction enzymes such as Hinfl and RsaI and run in agarose gels for transfer to Nytran filters. The filters are hybridized with a telomere specific probe such as $(TTAGGG)_3$. Autoradiographs are generated without an intensifying screen using the linear response range of the film and scanned with a densitometer. Output is digitized. Mean telomere length is defined as $\Sigma(OD_i)/\Sigma(OD_i/L_i)$ where $OD_i$ is the densitometer output (arbitrary units) and Li is the length of the DNA at position i. Sums are calculated over the range of 3-17 KB. This calculation assumes that DNA transfers at equal efficiency from all points in the gel and that the number of target sequences (telomere repeats) per DNA fragment is proportional to DNA length. The signal from the gels may be normalized to the signal from other Southern blots using a control probe in order to estimate the total amount of telomeric DNA as well as its length. (Harley et al., *Nature* 345:458-460 (1990), Englehardt et la., *Leukemia* 12:13-24 (1998)). This method also gives the size distribution of telomere lengths in the cell population from which the DNA was isolated. Since short telomeres are particularly susceptible to telomere dysfunction, modifications to the current invention could include calculations based on the mean or median telomere length of the short telomeres (e.g. for the shortest quartile of telomeres).

B. Polymerase Chain Reaction

Polymerase Chain Reaction (PCR) methods have been developed to measure average and chromosome specific telomere lengths. The first method provides a measure of telomeric DNA relative to genomic DNA (typically a single-copy gene) as a single ration value of a sample of genomic DNA (Cawthon R M, *Nucl. Acids Res*. Vol 30, pp e47).

In the Single Telomere Length Analysis (STELA) the telomere lengths from individual chromosomes are determined (Baird et al., *Nature Genetics* 33 203-207 (2003)). In this process, the DNA is digested with a restriction enzyme such as EcoRI and quantitated by Hoechst fluorometry. A linker or "telorette" comprising several bases complementary to the TTAGGG single-stranded region of the chromosome, preceded at the 5' end by a 20 nucleotides of unique sequence DNA. This telorette is annealed to the TTAGGG overhang at the end of the telomere and ligated to the 5'end of the complementary C-rich strand of the chromosome. This effectively tags the end of the telomere with a telorette tail that has a unique sequence capable of binding one of the PCR primers. Polymerase chain reaction (PCR) is then performed using a primer ("teltail") that is complementary to the telorette tail, together with a primer that is corresponds to the chromosome region adjacent to the telomere. The primer corresponding to the chromosome region adjacent to the telomere can also be made chromosome specific by exploiting chromosomal polymorphisms. After the PCR. The DNA fragments are resolved with agarose gel electrophoresis and detected by Southern blot hybridization with a random primed telomere adjacent probe. The size of the hybridized fragments can be determine from size standards on the gel and used to calculate the length of individual telomeres. This method also gives the size distribution of the telomeres from the specific chromosome targeted in the cell population from which the DNA was isolated. Since PCR biases amplification of short DNA fragments, STELA is particularly useful for analysis of the shortest telomeres in a cell. This has application to the current invention as described above.

C. Flow Cytometry and FISH Analysis

The average or median length of telomere repeats in calls can also be determined using fluorescent in situ hybridization (FISH) with labeled peptide nucleic acid (PNA) probes specific for telomere repeats in combination with fluorescence measurements by flow cytometry (flow FISH). (See Baerlocher et al., *Nature Protocols* vol. 1 2365-2376 (2006) incorporated by reference in its entirety). The advantage of Flow FISH is in providing multi-parameter information on the length of telomere repeats in thousands of individual cells. Automated multicolor flow FISH is one of the fastest and most sensitive methods available to measure the average or median telomere length in granulocytes, naïve T cells, memory T cells, B cells and natural killer (NK) cells in human blood. (Baerlocher and Lansdorp, *Methods in Cell boil.* 75, 719-750 (2004).

In flow FISH whole blood is centrifuged, red cells lysed and the red cell lysate separated from the cell pellet consisting of granulocytes, monocytes, lymphocytes, platelets and any remaining red cells. The white blood cell pellet is resuspended in a hybridization buffer and counted. The nucleated human blood cells are mixed with bovine thymocytes, included as an internal control as these cells are easily obtained and because the telomere length in bovine thymocytes is about 2-3 times longer than is typically measured in human cells. Accordingly these control cells are easily distinguished from the human test cells and provide a reference point for telomere fluorescence measurements. The mixture of human cells and bovine thymocytes is hybridized with the Cy5 or flourescein labeled PNA (peptide nucleic acid) probe which is complementary to the telomere repeat sequence. A second mixture of the cells is not hybridized with the probe. This latter is required to measure the level of autoflourescence in the cells of interest and to enable telomere length to be calculated from specific PNA hybridization. The fluorescein or Cy5 PNA probe is commercially available. After hybridization, the cells are pelleted and the cell pellet washed. The cells may be counter-stained with non-saturating concentrations of a DNA dye and various antibodies. The cell samples are run on a flow cytometer.

The first step in the subsequent analysis is to identify cells using forward light and side scatter in a bivariate dot plot. Three cell populations can be observed. The bovine thymocytes can be distinguished from the human lymphocytes which in turn can be distinguished from the granulocytes. By combining the fluorescence in the contour plots fluorescence histograms of the different cell populations can be obtained, which are used for subsequence calculations of telomere length. Antibodies specific for CD45RA and CD20 cells can be used to perform telomere length analysis of specific populations within the lymphocyte population. The average telomere length can be determined by subtracting the flouresence of the unstained white blood cell populations from the level of fluorescence of the PNA stained cells. This method collects an average telomere signal from each individual cell, thus the telomere size distribution of the overall population can be obtained, and one could analyze the subset of cells with short telomeres. This has application to the current invention as described above.

2. Algorithm to Predict the Platelet Levels, or Changes Alter Telomerase Inhibition Therapy and to Generate Likelihood of Adverse Reaction An aspect of the present invention is to use the measured average length of the telomeres in the cells from the patient to provide information regarding the likelihood of an adverse reaction to a telomerase inhibitor prior to administration of a telomerase inhibitor.

In the next step the measured average telomere length is multiplied by a coefficient reflecting its relative contribution to the risk of the adverse reaction to treatment with a telomerase inhibitor to determine the telomere length component.

The next step is to take the intended dosage of the telomerase inhibitor and multiply the dosage by a coefficient reflecting its relative contribution to the risk of the adverse reaction to treatment with a telomerase inhibitor to determine the dosage component.

The telomere length component and the dosage component are added with an intercept factor to determine the likelihood of the adverse reaction.

For example, the equation to describe the predicted number of platelets at platelet nadir in a patient after 4 complete weeks of treatment is as follows:

Predicted # of platelets=baseline platelets number−(baseline platelet number×% change in platelets/100).

% change in platelet #=(−73.8)−6.6×inhibitor dose (mg/kg)+11.2×average telomere length (kbp)

The equation to describe the predicted number of platelets at platelet nadir in a patient during first 4 weeks of treatment is as follows:

Predicted # of platelets=$e^{[(-0.38)-0.13 \times inhibitor\ dose\ (mg/kg)+0.25 \times average\ telomere\ length\ (kbp)+0.80 \times log\ of\ baseline\ platelet\ number]}$ Prediction intervals may be calculated for example, to predict likely percent change in platelet levels or the platelet nadir for patients or subjects with a particular set of baseline and treatment values, for example, telomere length, baseline platelets and dose level. The regression equation provides the expected value for a future individual with specified covariates (J. Neter et al. *Applied linear statistical models: regression, analysis of variance, and experimental designs,*

3rd edition pp. 81-83 (1990)). However, due to sampling distribution error as well as interindividual variability, a patient may have platelet levels that fall above or below that predicted value. A series of prediction intervals may be created with decreasing coverage. For example, a 99% prediction interval with upper and lower bounds $P_{U99}$ and $P_{L99}$ may be created and would, on average, contain 99% of the patients' observed platelet levels. A 90% prediction interval with upper and lower bounds $P_{U90}$ ($<P_{U99}$) and $P_{L90}$ ($>P_{L99}$) may be created and would, on average, contain 90% of future observed platelet levels. This allows one to determine the likelihood that the patient would develop a grade 3 or 4 thrombocytopenia.

The likelihood of risk of an adverse reaction, as determined by the algorithm of the present invention, provides valuable tools for the practicing physician to make critical treatment decisions. Thus if the risk of a particular patient is low, the physician might decide that following surgical removal of the cancer the patient can be treated aggressively with high doses and high frequency of administration of the telomerase inhibitor. If, on the other hand the level of risk is determined to be high, this information can be used to decide the level of dose of the telomerase inhibitor to administer, the regimen of dosing to use, including the use of weeks with no dose administered, so called "resting" weeks. The physician may decide to monitor the patient more closely for adverse reactions, such as thrombocytopenia. The physician may decide to administer an ameliorating pharmaceutical concurrently with the telomerase inhibitor. If the risk of the patient for an adverse reaction is high, other treatment modalities may be used to combat cancer in that particular patient. Other treatment modalities for a particular cancer include, for example, other chemotherapies such as anthracycline and/or taxane based treatments, HER inhibitors, EGFR inhibitors and/or other treatment options, such as radiation therapy alone, before or after chemotherapy.

3. Telomerase Inhibitors and Treatment of Cancer with a Telomerase Inhibitor

Telomerase is a ribonucleoprotein that catalyzes the addition of telomeric repeat sequences (having the sequence 5'-TTAGGG-3' in humans) to chromosome ends. A variety of cancer cells have been shown to be telomerase-positive, including cells from cancer of the skin, connective tissue, adipose, breast, lung, stomach, pancreas, ovary, cervix, uterus, kidney, bladder, colon, prostate, central nervous system (CNS), retina and hematologic tumors (such as myeloma, leukemia and lymphoma). Targeting of telomerase can be effective in providing treatments that discriminate between malignant and normal cells to a high degree, avoiding many of the deleterious side effects that can accompany chemotherapeutic regimens which target dividing cells indiscriminately.

Inhibitors of telomerase identified to date include oligonucleotides, preferably oligonucleotides having nuclease resistant linkages, as well as small molecule compounds.

A. Small Molecule Compounds

Small molecule inhibitors of telomerase include, for example, BRACO19 ((9-(4-(N,N-dimethylamino)phenylamino)-3,6-bis(3-pyrrolodino propionamido)acridine (see *Mol. Pharmacol.* 61(5):1154-62, 2002); DODC (diethyloxadicarbocyanine), and telomestatin. These compounds may act as G-quad stabilizers, which promote the formation of an inactive G-quad configuration in the RNA component of telomerase. Other small molecule inhibitors of telomerase include BIBR1532 (2-[(E)-3-naphthen-2-yl but-2-enoylamino]benzoic acid) (see Ward & Autexier, *Mol. Pharmacol.* 68:779-786, 2005; also *J. Biol. Chem.* 277(18):15566-72, 2002); AZT and other nucleoside analogs, such as ddG and ara-G (see, for example, U.S. Pat. Nos. 5,695,932 and 6,368,789), and certain thiopyridine, benzo[b]thiophene, and pyrido[b]thiophene derivatives, described by Gaeta et al. in U.S. Pat. Nos. 5,767,278, 5,770,613, 5,863,936, 5,656,638 and 5,760,062. One example is 3-chlorobenzo[b]thiophene-2-carboxy-2'-[(2,5-dichlorophenyl amino)thia]hydrazine, described in U.S. Pat. No. 5,760,062.

B. Oligonucleotide-Based Telomerase Inhibitors: Sequence and Composition

The genes encoding both the protein and RNA components of human telomerase have been cloned and sequenced (see U.S. Pat. Nos. 6,261,836 and 5,583,016, respectively, both of which are incorporated herein by reference). Oligonucleotides can be targeted against the mRNA encoding the telomerase protein component (the human form of which is known as human telomerase reverse transcriptase, or hTERT) or the RNA component of the telomerase holoenzyme (the human form of which is known as human telomerase RNA, or hTR). U.S. Pat. Nos. 5,583,016; 5,776,679; 5,837,857 which are incorporated herein by reference.

The template sequence of the RNA component of telomerase is located within the region defined by nucleotides 46-56 (5'-CUAACCCUAAC-3') (SEQ ID NO: 1), which is complementary to a telomeric sequence composed of about one-and-two-thirds telomeric repeat units. The template region functions to specify the sequence of the telomeric repeats that telomerase adds to the chromosome ends and is essential to the activity of the telomerase enzyme (see e.g. Chen et al., *Cell* 100: 503-514, 2000; Kim et al., *Proc. Natl. Acad. Sci. USA* 98 (14):7982-7987, 2001). The design of antisense, ribozyme or small interfering RNA (siRNA) agents to inhibit or cause the destruction of mRNAs is well known (see, for example, Lebedeva, I, et al. Annual Review of Pharmacology and Toxicology, Vol. 41: 403-419, April 2001; Macejak, D, et al., Journal of Virology, Vol. 73 (9): 7745-7751, September 1999, and Zeng, Y. et al., PNAS Vol. 100 (17) p. 9779-9784, Aug. 19, 2003) and such agents may be designed to target the hTERT mRNA and thereby inhibit production of hTERT protein in a target cell, such as a cancer cell (see, for example, U.S. Pat. Nos. 6,444,650 and 6,331,399).

Oligonucleotides targeting hTR (that is, the RNA component of the enzyme) act as inhibitors of telomerase enzyme activity by blocking or otherwise interfering with the interaction of hTR with the hTERT protein, which interaction is necessary for telomerase function. See, for example, Villeponteau et al., U.S. Pat. No. 6,548,298.

A preferred target region of hTR is the template region, spanning nucleotides 30-67 of the RNA component of human telomerase. Oligonucleotides targeting this region are referred to herein as "hTR template inhibitors" (see e.g. Herbert et al., *Oncogene* 21(4):638-42 (2002).) Preferably, such an oligonucleotide includes a sequence which is complementary or near-complementary to some portion of the 11-nucleotide region having sequence 5'-CUAACCCUAAC-3' (SEQ ID NO:1), spanning nucleotides 46-56 of the RNA component of human telomerase (hTR).

Another preferred target region is the region spanning nucleotides 137-179 of human telomerase (hTR) (see Pruzan et al., *Nucl. Acids Research*, 30:559-568, 2002). Within this region, the sequence spanning 141-153 is a preferred target. PCT publication WO 98/28442 describes the use of oligonucleotides of at least 7 nucleotides in length to inhibit telomerase, where the oligonucleotides are designed to be complementary to accessible portions of the hTR sequence outside of the template region, including nucleotides 137-196, 290-319, and 350-380 of hTR.

The region of the therapeutic oligonucleotide that is targeted to the hTR sequence is preferably exactly complementary to the corresponding hTR sequence. While mismatches may be tolerated in certain instances, they are expected to decrease the specificity and activity of the resultant oligonucleotide conjugate. In particular embodiments, the base sequence of the oligonucleotide is thus selected to include a sequence of at least 5 nucleotides exactly complementary to the hTR target, and enhanced telomerase inhibition may be obtained if increasing lengths of complementary sequence are employed, such as at least 8, at least 10, at least 12, at least 13 or at least 15 nucleotides exactly complementary to the hTR target. In other embodiments, the sequence of the oligonucleotide includes a sequence of from at least 5 to 20, from at least 8 to 20, from at least 10 to 20 or from at least 10 to 15 nucleotides exactly complementary to the hTR target sequence.

Optimal telomerase inhibitory activity may be obtained when the full length of the oligonucleotide is selected to be complementary to the hTR target sequence. However, it is not necessary that the full length of the oligonucleotide is exactly complementary to the target sequence, and the oligonucleotide sequence may include regions that are not complementary to the target sequence. Such regions may be added, for example, to confer other properties on the compound, such as sequences that facilitate purification. Alternatively, an oligonucleotide may include multiple repeats of a sequence complementary to an hTR target sequence.

The method includes administering to the subject an oligonucleotide telomerase inhibitor of the type composed of an oligonucleotide having nuclease-resistant intersubunit linkages and an oligonucleotide sequence effective to bind by sequence-specific hybridization to a template region of hTR. Preferably, the amount of the telomerase inhibitor is effective to inhibit the proliferation of cancer cells in the subject when the telomerase inhibitor is administered alone.

The oligonucleotide may be 10-20 bases in length. Preferably, the oligonucleotide is 13-20 bases in length and includes the sequence (5'-TAGGGTTAGACAA-3') (SEQ ID NO:2). An exemplary telomerase inhibitor is the compound identified as GRN163L, or an analog thereof. This compound has (i) N3'→P5' thiophosphoramidate internucleoside linkages; (ii) the sequence 5'-TAGGGTTAGA-CAA-3'(SEQ ID NO:2); and (iii) a palmitoyl (C16) moiety linked to the 5' end of the oligonucleotide through a glycerol or aminoglycerol linker.

The internucleoside linkages in the oligonucleotide may include any of the available oligonucleotide chemistries, e.g. phosphodiester, phosphotriester, methylphosphonate, P3'→N5' phosphoramidate, N3'→P5' phosphoramidate, N3'→P5' thiophosphoramidate, and phosphorothioate. Typically, but not necessarily, all of the internucleoside linkages within the oligonucleotide will be of the same type, although the oligonucleotide component may be synthesized using a mixture of different linkages.

In preferred embodiments, the oligonucleotide has at least one N3'→P5' phosphoramidate (NP) or N3'→P5' thiophosphoramidate (NPS) linkage, which linkage may be represented by the structure: 3'-(-NH—P(=O)(—XR)—O-)-5', wherein X is O or S and R is selected from the group consisting of hydrogen, alkyl, and aryl; and pharmaceutically acceptable salts thereof, when XR is OH or SIH. More preferably, the oligonucleotide includes all NP or, most preferably, all NPS linkages.

A particularly preferred sequence for an hTR template inhibitor oligonucleotide is the sequence complementary to nucleotides 42-54 of the hTR. The oligonucleotide having this sequence (TAGGGTTAGACAA) (SEQ ID NO:2) and N3'→P5' thiophosphoramidate (NPS) linkages is designated herein as GRN163. See, for example, Asai et al., *Cancer Research* 63:3931-3939 (2003); Gryaznov et al., *Nucleosides Nucleotides Nucleic Acids* 22(5-8):577-81 (2003).

These compounds may be prepared as described, for example, in McCurdy et al., *Tetrahedron Letters* 38:207-210 (1997) or Pongracz & Gryaznov, *Tetrahedron Letters* 49:7661-7664 (1999). The starting 3'-amino nucleoside monomers may be prepared as described in Nelson et al., *J. Org. Chem.* 62:7278-7287 (1997) or by the methods described in Gryaznov et al., US Appn. Pubn. No. 2006/0009636.

A variety of synthetic approaches can be used to conjugate a lipid moiety L to the oligonucleotide, depending on the nature of the linkage selected; see, for example, Mishra et al., *Biochim. et Biophys. Acta* 1264:229-237 (1995), Shea et al., *Nucleic Acids Res.* 18:3777-3783 (1995), or Rump et al., *Bioconj. Chem.* 9:341-349 (1995). Typically, conjugation is achieved through the use of suitable functional groups at an oligonucleotide terminus. For example, the 3'-amino group present at the 3'-terminus of the NP and NPS oligonucleotides can be reacted with carboxylic acids, acid chlorides, anhydrides and active esters, using suitable coupling catalysts, to form an amide linkage. Thiol groups are also suitable as functional groups (see Kupihar et al., *Bioorg. Med. Chem.* 9:1241-1247 (2001)). Various amino- and thiol-functionalized modifiers of different chain lengths are commercially available for oligonucleotide synthesis.

Specific approaches for attaching lipid groups to a terminus of an NP or NPS oligonucleotide include those described in US Appn. Pubn. No. 2005/0113325, which is incorporated herein by reference. In addition to the amide linkages noted above, for example, lipids may also be attached to the oligonucleotide chain using a phosphoramidite derivative of the lipid, to produce a phosphoramidate or thiophosphoramidate linkage connecting the lipid and the oligonucleotide. The free 3'-amino group of the fully protected support-bound oligonucleotide may also be reacted with a suitable lipid aldehyde, followed by reduction with sodium cyanoborohydride, which produces an amine linkage.

The oligonucleotide GRN163 administered alone has shown inhibitory activity in vitro in cell culture, including epidermoid carcinoma, breast epithelium, renal carcinoma, renal adenocarcinoma, pancreatic, brain, colon, prostate, leukemia, lymphoma, myeloma, epidermal, cervical, ovarian and liver cancer cells.

The oligonucleotide GRN163 has also been tested and shown to be therapeutically effective in a variety of animal tumor models, including ovarian and lung, both small cell and non-small cell.

C. Lipid-Oligonucleotide Conjugates

Preferably, the oligonucleotide-based enzyme inhibitor includes at least one covalently linked lipid group (see US Publication. No. 2005/0113325, which is incorporated herein by reference). This modification provides superior cellular uptake properties, such that an equivalent biological effect may be obtained using smaller amounts of the conjugated oligonucleotide compared to the unmodified form. When applied to the human therapeutic setting, this may translate to reduced toxicity risks, and cost savings.

The lipid group L is typically an aliphatic hydrocarbon or fatty acid, including derivatives of hydrocarbons and fatty acids, with examples being saturated straight chain compounds having 14-20 carbons, such as myristic (tetradecanoic) acid, palmitic (hexadecanoic) acid, and stearic (octadeacanoic) acid, and their corresponding aliphatic hydrocarbon forms, tetradecane, hexadecane and octadecane. Examples of other suitable lipid groups that may be employed are sterols, such as cholesterol, and substituted fatty acids and hydrocarbons, particularly polyfluorinated forms of these groups. The scope of the lipid group L includes derivatives such as amine, amide, ester and carbamate derivatives. The type of derivative is often determined by the mode of linkage to the oligonucleotide, as exemplified below.

In one exemplary structure, the lipid moiety is palmitoyl amide (derived from palmitic acid), conjugated through an aminoglycerol linker to the 5' thiophosphate group of an NPS-linked oligonucleotide. The NPS oligonucleotide having the sequence shown for GRN163 and conjugated in this manner (as shown below) is designated GRN163L herein. In a second exemplary structure, the lipid, as a palmitoyl amide, is conjugated through the terminal 3' amino group of an NPS oligonucleotide.

GRN163L

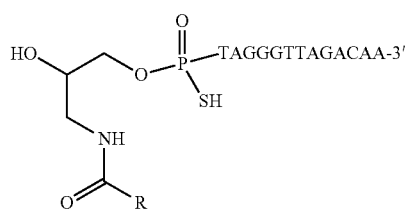

R = —(CH$_2$)$_{14}$CH$_3$ (palmitoyl)

For attachment of a lipid to the 5' terminus, as also described in US Appn. Pubn. No. 2005/0113325, the oligonucleotide can be synthesized using a modified, lipid-containing solid support. Reaction of 3-amino-1,2-propanediol with a fatty acyl chloride (RC(O)Cl), followed by dimethoxytritylation of the primary alcohol and succinylation of the secondary alcohol, provides an intermediate which is then coupled, via the free succinyl carboxyl group, to the solid support. An example of a modified support is shown below, where S— represents a long chain alkyl amine CPG support, and R represents a lipid.

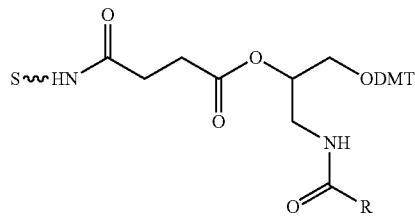

This procedure is followed by synthesis of the oligonucleotide in the 5' to 3' direction, as described, for example, in Pongracz & Gryaznov (1999), starting with de-protection and phosphitylation of the —ODMT group. This is effective to produce, for example, the following structure, after cleavage from the solid support:

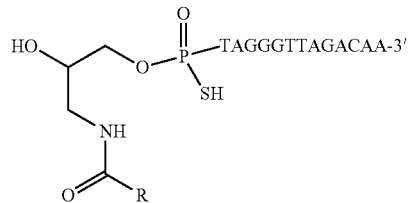

The structure above, when —R is —(CH$_2$)$_{14}$CH$_3$ (palmitoyl), is designated herein as GRN163L.

IV. Administration

The cancer should also be one that is responsive to cancer-cell inhibition by telomerase inhibition. As noted above, oligonucleotide telomerase inhibitors, as exemplified by GRN163 and GRN163L, have shown inhibitory activity in vitro against human kidney, lung, pancreatic, brain, colon, prostate, breast, leukemia, lymphoma, myeloma, epidermal, cervical, ovarian and liver cancer cells, and in vivo, via local and systemic delivery, against human brain, prostate, lymphoma, myeloma, cervical, lung, and liver cancer cells. Other preferred targets include small cell lung, esophageal, head and neck, and stomach cancers.

The dose administered and the dosing schedule will follow, for example, known or recommended doses for the inhibitor employed, as indicated, for example, in the drug product insert or published clinical or animal-model data. For GRN163L, the adult starting dose is from about 0.8 mg/kg to about 50 mg/kg; from about 1.6 mg/kg to about 20 mg/kg. The adult dose for GRN163L is from about 1.6 mg/kg; or about 3.2 mg/kg; or about 4.8 mg/kg; or about 6.2 mg/kg; or about 7.2 mg/kg; or about 9 mg/kg; or about 12 mg/kg; to about 20 mg/kg. The dose may be administered twice weekly, once weekly or at other rates of administration. Higher doses may be required to produce the desired remission in some patients.

GRN163L may be administered to a patient at a dose of at least about 4.8 mg/kg of GRN163L on day 1 and on approximately day 8 of a 21 day cycle. Alternatively it may be administered at a dose of at least about 4.8 mg/kg of GRN163L on day 1 and on approximately day 15 of a 28 day cycle. Alternatively, GRN163L may be administered to a patient at a dose of at least about 1.6 mg/kg of GRN163L two times in the first week of a 14 day cycle.

The therapeutic protocol for administering the telomerase inhibitor in the therapy will depend on various factors including, but not limited to, the type of cancer, the age and general health of the patient, the aggressiveness of disease progression, the telomere length and telomerase activity of the diseased cells to be treated, and the ability of the patient to tolerate the agents that comprise the combination, which may depend upon telomerase activity and telomere length in various normal cells, particularly normal cells in highly proliferative tissues, particularly, but not limited to, the bone marrow.

In general, treatment of all cancer and hematological malignancy types is contemplated. In selected embodiments, the target disease comprises a solid tumor; in other embodiments, the target disease comprises a hematological malignancy. An exemplary course of treatment involves multiple doses. Sequence of combination treatments will be determined by clinical compliance criteria and/or preclinical or clinical data supporting dose optimization strategies to augment efficacy or reduce toxicity of the combination treatment. The time between dosages may be for a period from about 1-6 hours, to about 6-12 hours, to about 12-24 hours, to about 1-2 days, to about 1-2 wk or longer following the initiation of treatment. During a course of treatment, the need to complete the planned dosings may be re-evaluated.

The compounds may be administered by direct injection of a tumor or its vasculature. Alternatively, the tumor may be infused or perfused with the therapeutic compounds using any suitable delivery vehicle. The compounds may be administered locally to an affected organ. Systemic administration may also be performed. Continuous administration may be applied where appropriate; for example, where a tumor is excised and the tumor bed is treated to eliminate residual disease. Delivery via syringe or catheterization is preferred. Such continuous perfusion may take place for a period from about 1-6 hours, to about 6-12 hours, to about 12-24 hours, to about 1-2 days, to about 1-2 weeks or longer following the initiation of treatment. Generally, the dose of the therapeutic composition via continuous perfusion will be equivalent to that given by a single or multiple injections, adjusted over a period of time during which the perfusion occurs.

The therapeutic agents are administered to a subject, such as a human patient, in a formulation and in an amount effective to achieve a clinically desirable result. For the treatment of cancer, desirable results include reduction in tumor mass (as determined by palpation or imaging; e.g., by radiography, radionucleotide scan, CAT scan, or MRI), reduction in the rate of tumor growth, reduction in the rate of metastasis formation (as determined e.g., by histochemical analysis of biopsy specimens), reduction in biochemical markers (including general markers such as ESR, and tumor specific markers such as serum PSA), and improvement in quality of life (as determined by clinical assessment, e.g., Karnofsky score), increased time to progression, disease-free survival and overall survival.

The amount of each agent per dose and the number of doses required to achieve such effects will vary depending on many factors including the disease indication, characteristics of the patient being treated and the mode of administration. Typically, the formulation and route of administration will provide a local concentration at the disease site of between 1 nM and 100 µM of each agent. The physician will be able to vary the amount of the compounds, the carrier, the dosing frequency, and the like, taking into consideration such factors as the particular neoplastic disease state and its severity; the overall condition of the patient; the patient's age, sex, and weight; the mode of administration; the suitability of concurrently administering systemic anti-toxicity agents; monitoring of the patient's vital organ functions; and other factors typically monitored during cancer chemotherapy. In general, the compounds are administered at a concentration that affords effective results without causing excessive harmful or deleterious side effects.

Modes of administration and formulation may be dependent on the drug and its approved mode of administration. When the telomerase inhibitor is GRN163L, formulation in 0.9% sodium chloride (normal saline) and administration by i.v. is a preferred route, preferably via infusion over 1 to 24 hours, more preferably over 2 to 8 hours, e.g. a 6 hr infusion. While the lipid-conjugated oligonucleotides described herein, such as GRN163L, have superior characteristics for cellular and tissue penetration, these and other compounds may be formulated to provide further benefit in this area. Other useful adjuvants include substrates for transendothelial migration, such as glucose uptake systems for facilitated egress from the vascular space to the tumor microenvironment.

The following examples are offered by way of illustration and not by way of limitation.

EXAMPLES

Example 1

Study of Various Parameters in Patients Prescribed Telomerase Inhibitors

A study was designed and conducted to determine the likelihood of development of thrombocytopenia in a population of solid tumor cancer patients being treated with the telomerase inhibitor GRN163L. GRN163L is a 13-mer oligonucleotide inhibitor of telomerase activity. The study utilized archived blood cells as a source of cellular telomere length before the study and matched archived patient records.

Study Design

The patents accepted were adults with refractory, advanced solid tumors and treated with GRN163L in a phase T clinical trail. The GRN163L was given by continuous weekly i.v. dosing. In addition interim data are presented on a cohort 6 treated with an alternative dosing regimen of designed to reduce the potential for thrombocytopenia. This was a multicenter Phase I clinical trial with sequential cohorts of dose escalation. Patients were enrolled in successive cohorts at 0.4 to 4.8 mg/kg. Cohorts 1-5 received 2 hr intravenous infusions of GRN163L weekly. Cohort 6 received an intermittent dosing schedule of weekly iv infusions of GRN163L (4.8 mg/kg)×2, followed by a 13 day rest. Completion of 1 cycle (4 weekly infusions) was required for Dose Limiting Toxicity (DLT) evaluation Patients were excluded from the study if they had a primary malignancy or active metastasis in the Central Nervous System; hematologic malignancies; hemoglobin<9.0 g/dL; ANC<1,500/mm3; platelet count<100,000/mm3; or a serum chemistry abnormality (bilirubin, AST, ALT, albumin, creatinine).

The patient population included 28 patients. Patients had received up to 9 prior therapies for this tumor; more than half received 4 or more. See Table 1

TABLE 1

| Demographics at Baseline | |
|---|---|
| # of Patients | 28 |
| Male | 20 |
| Female | 8 |
| Age; Median (years) | 63 |
| Range 31 | 76 |
| Karnofsky | Status |
| 70-80 | 16 |
| 90-100 | 12 |
| Stage 3 | 1 |
| Stage 4 | 26 |
| Unknown | 1 |
| Primary Tumor Site Lung | |
| Lung | 3 |
| Pleura | 2 |
| Gastro | |
| Esophagus | 1 |
| Stomach | 1 |
| Pancreas | 4 |
| Liver | 2 |
| Colon | 5 |
| Rectal | 3 |

TABLE 1-continued

Demographics at Baseline

Primary Tumor Site
Other

| | |
|---|---|
| Bone | 1 |
| Breast | 1 |
| Oropharnyx | 1 |
| Parathyroid | 1 |
| Prostate | 1 |
| Skin | 1 |
| Testicular | 1 |

28 patients in Cohorts 1-5 received at least 1 infusion of GRN163L. A total of 177 doses were administered. See Table 2. All 28 patients discontinued the study; reasons for discontinuation included progressive disease (22/28; 78%), death (3/28; 11%) and thrombocytopenia (3/28; 11%).

TABLE 2

Dosing

| | Cohorts | | | | | |
|---|---|---|---|---|---|---|
| | 1 | 2 | 3 | 4 | 5 | Total |
| Dose (mg/kg) | 0.4 | 0.8 | 1.6 | 3.2 | 4.8 | — |
| # of Patients | 2 | 2 | 2 | 8 | 14 | 28 |
| Median # of Cycles/patient | 3.0 | 3.0 | 1.5 | 1.5 | 2.0 | 2.0 |
| Median # of Doses/patient | 11.5 | 12.0 | 5.5 | 5.5 | 5.5 | 7.0 |
| Percent of doses Received | 100% | 100% | 100% | 81% | 84% | 88% |

Blood samples were taken from the patients at different times during the study. FIGS. 1-4 show the platelet levels in the patients over time in the various cohorts.

Materials and Methods:

Blood samples were collected from each patient prior to starting treatment. Median telomere length was determined by Repeat Diagnostics, Vancouver Canada using the Flow-FISH method, with gating on granulocyte and lymphocyte populations by the method described in Baerlocher et al., "Flow cytometry and FISH to measure the average length of telomeres (flow FISH) *Nature Protocols* Vol. 1, No. 5: 2365-2376 (2006) which is incorporated by reference herein in its entirety Briefly, whole blood from the 28 patients were. The supernatant was aspirated without disturbing the white blood cell or red blood cell pellet. The cells were mixed with cold $NH_4Cl$ to lyse the red blood cells. The cells were centrifuged. The supernatant was aspirated and the red cell lysate removed. The resulting white blood cells were suspended in Hybridization Buffer (5% dextrose/10 mM Hepes/0/1% BSA). The cells were counted and diluted to approximately $5 \times 10^6$ cells/200 μl of Hybridization Buffer.

Bovine thymocytes were isolated from fresh bovine thymus and fixed in formaldehyde. The fixed bovine thymocytes were mixed with Hybridization buffer (Tris, NaCl, BSA, dionized formamide). For the unlabeled hybridization control, unlabeled hybridization mix stock was added to the cells. For the Labeled Hybridization Mixture, hybridization Peptide nucleic acid (PNA) probe (Cy5 or flourescein labeled CCC TAA CCC TAA CCC TAA) (SEQ ID NO:3) was added to the cells. The cells were hybridized with the PNA probe. Then the cells were centrifuged and the cell pellet was washed to remove unbound probe.

The flow cytometer was calibrated and the cells run on the flow cytometer. From the flow cytometry data analysis software program, the flow FISH analysis template was used to calculate the fluorescence of the various cell populations. The flourescence was used to calculate the average telomere length.

Results

Univariate and multivariate analyses were undertaken to explore predictive factors for post-treatment decreases in platelet levels and baseline telomere length. Factors included age, sex, baseline platelet counts, time since cancer diagnosis, number of prior cytotoxic or myelosuppressive chemotherapy regimens, prior radiation therapy, and baseline granulocyte and lymphocyte telomere length.

Infusions of GRN163L were generally well tolerated. Adverse events (AE) that were considered to be related or possibly/probably related to treatment were reported in 16/28 (57.1%) patients. See Table 3. Most possibly/probably related adverse events were reversible and Grade 1-2.

No dose limiting toxicities (DLT) were observed in Cohorts 1-3. In Cohort 4 (3.2 mg/kg), a patient who was tolerating therapy well died of unknown cause after the 4th dose, and this was considered a DLT. In Cohort 5 (4.8 mg/kg), two DLTs were observed—both thrombocytopenia (one grade 4 and one grade 2 causing a >2 week delay in treatment).

TABLE 3

Reported adverse events (Possibly/Probably) Related to Treatment in >1 patient†

| | Dose (mg/kg) | | | |
|---|---|---|---|---|
| | 0.4-1.6 | 3.2 | 4.8 | Total |
| # of Patients | 6 | 8 | 14 | 28 |
| Reported at least 1 AE | 2 (33.3%) | 8 (100%) | 13 (92.9%) | 23 (82.1%) |
| Activated partial thromboplastin time prolonged | | | | |
| Grade 1-2 | 0 | 6 (75%) | 6 (42.9%) | 12 (42.9%) |
| Grade 3 | 0 | 0 | 6 (42.9%) | 6 (21.4%) |
| Thrombocytopenia‡ | | | | |
| Grade 1-2 | 0 | 1 (12.5%) | 3 (21.4%) | 4 (14.3%) |
| Grade 3-4 | 0 | 1 (12.5%) | 2 (14.3%) | 3 (10.7%) |
| Anemia—Grade 2-3 | 0 | 1 (12.5%) | 2 (14.3%) | 3 (10.7%) |
| Leukopenia—Grade 1-3 | 0 | 0 | 2 (14.3%) | 2 (7.1%) |
| Neutropenia—Grade 2-3 | 0 | 0 | 2 (14.3%) | 2 (7.1%) |

†Adverse events in 1 patient only included photophobia, peripheral neuropathy, sedimentation rate elevated, increased alkaline phosphotase, lymphopenia, tenderness at neck above port site, burning on urination, candidiasis, chest tightness, confusion, dehydration, elevated AST and death.
‡Not all lab readings consistent with thrombocytopenia were reported as adverse events.

Figure 2:
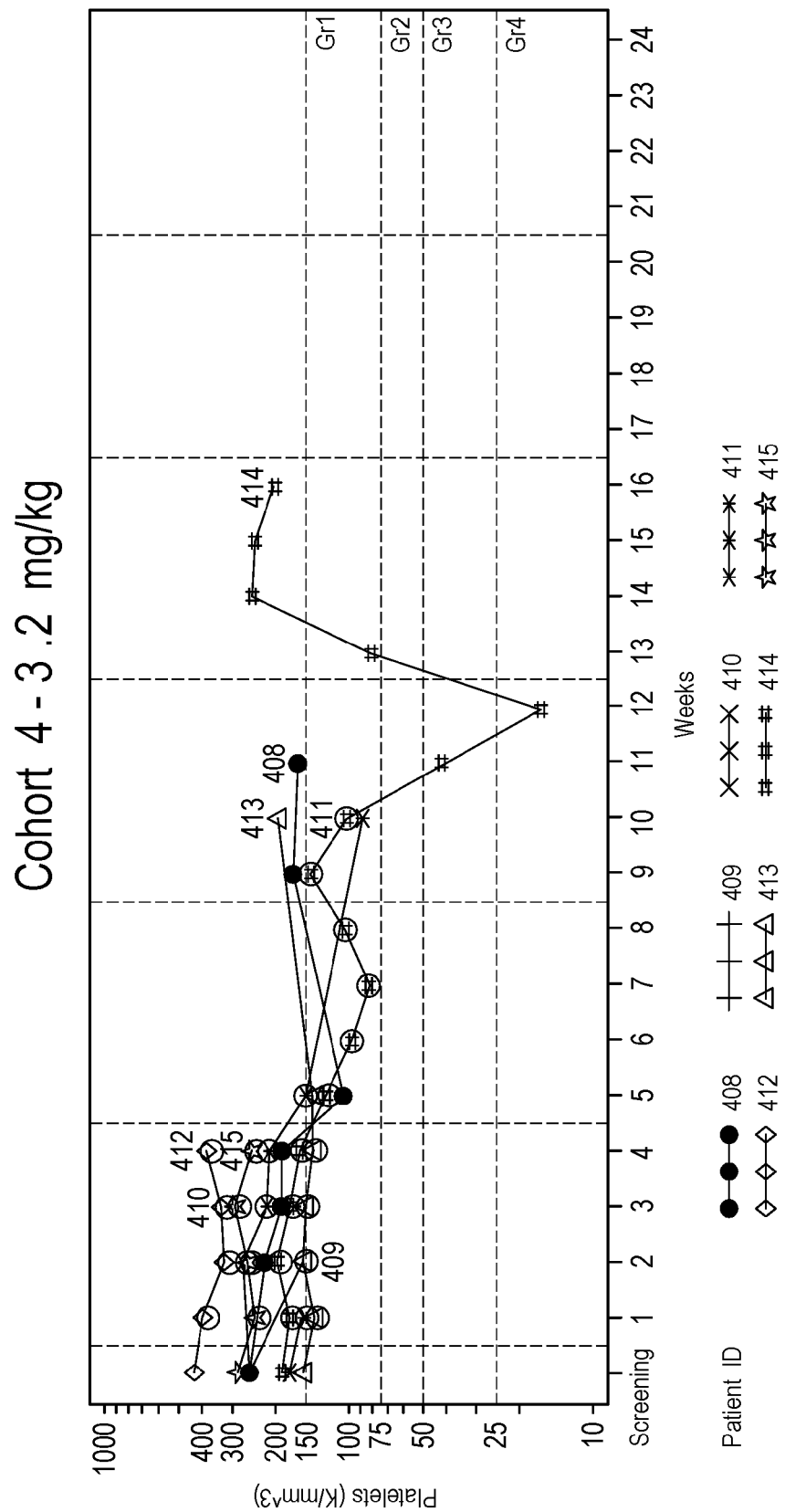
FIG. 2 is a graph showing platelet levels over time for individual patients in cohort 4 of the study. Broken horizontal lines show the ranges for different levels of thrombocytopenia. Circles at time points indicate that the patients received a dose of GRN163L and platelets were collected.
Figure 3:
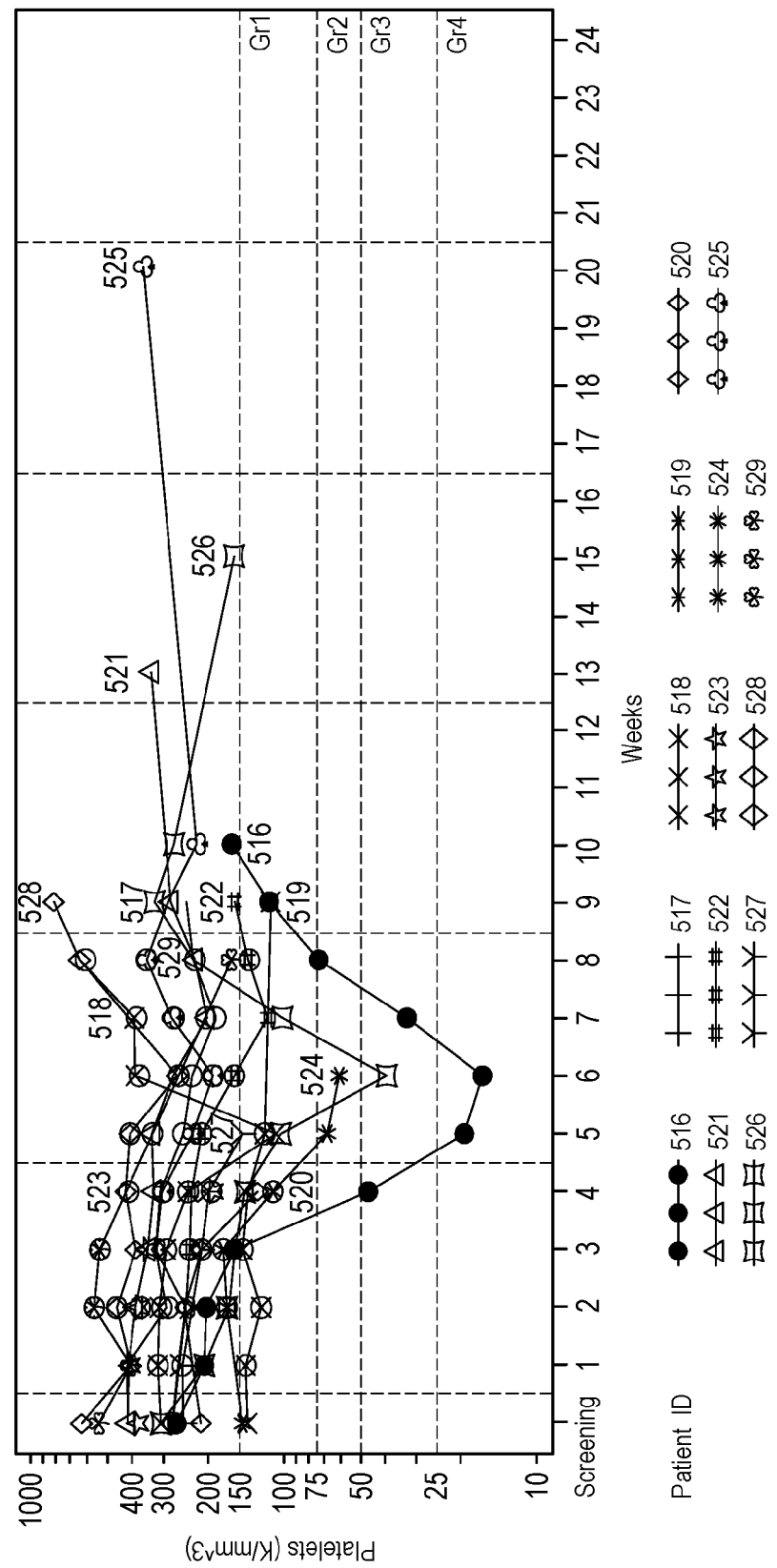
FIG. 3 is a graph showing platelet levels over time for individual patients in cohort 5 of the study. Broken horizontal lines show the ranges for different levels of thrombocytopenia. Circles at time points indicate that the patients received a dose of GRN163L and platelets were collected.
Figure 4:
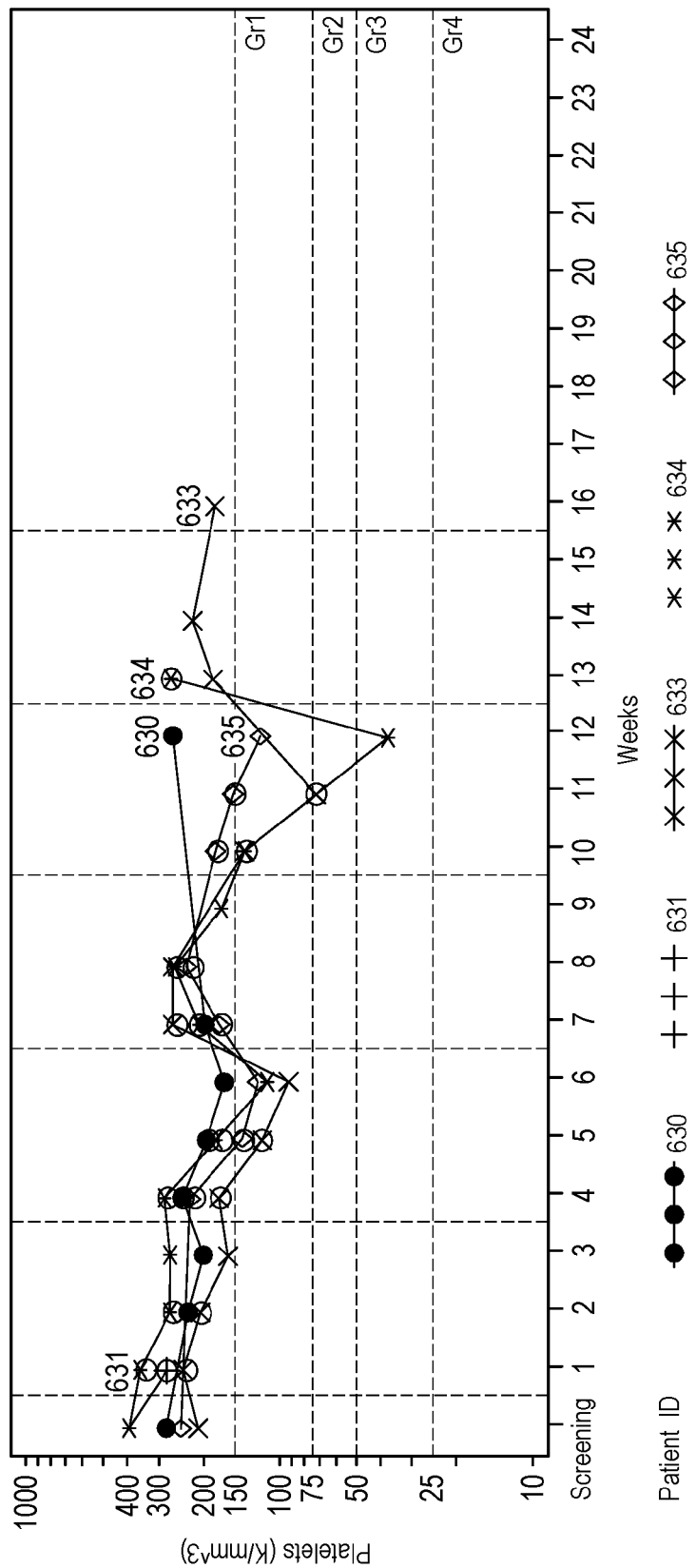
FIG. 4 is a graph showing platelet levels over time for individual patients in cohort 6 of the study. Broken horizontal lines show the ranges for different levels of thrombocytopenia. Circles at time points indicate that the patients received a dose of GRN163L and platelets were collected.

Platelet levels over time for individual patients receiving weekly infusions of GRN163L are shown by dose cohort in FIGS. 1-3. Circled data points indicate that the patient received treatment at that visit. Platelet levels over time for 5 of 6 patients on the intermittent 4.8 mg/kg dosing schedule (Cohort 6) are shown in FIG. 4.

To better understand patient and treatment factors potentially influencing platelet declines (or increases), a model was developed to identify predictors of percent change in platelet levels at 4 weeks.

Figure 5:
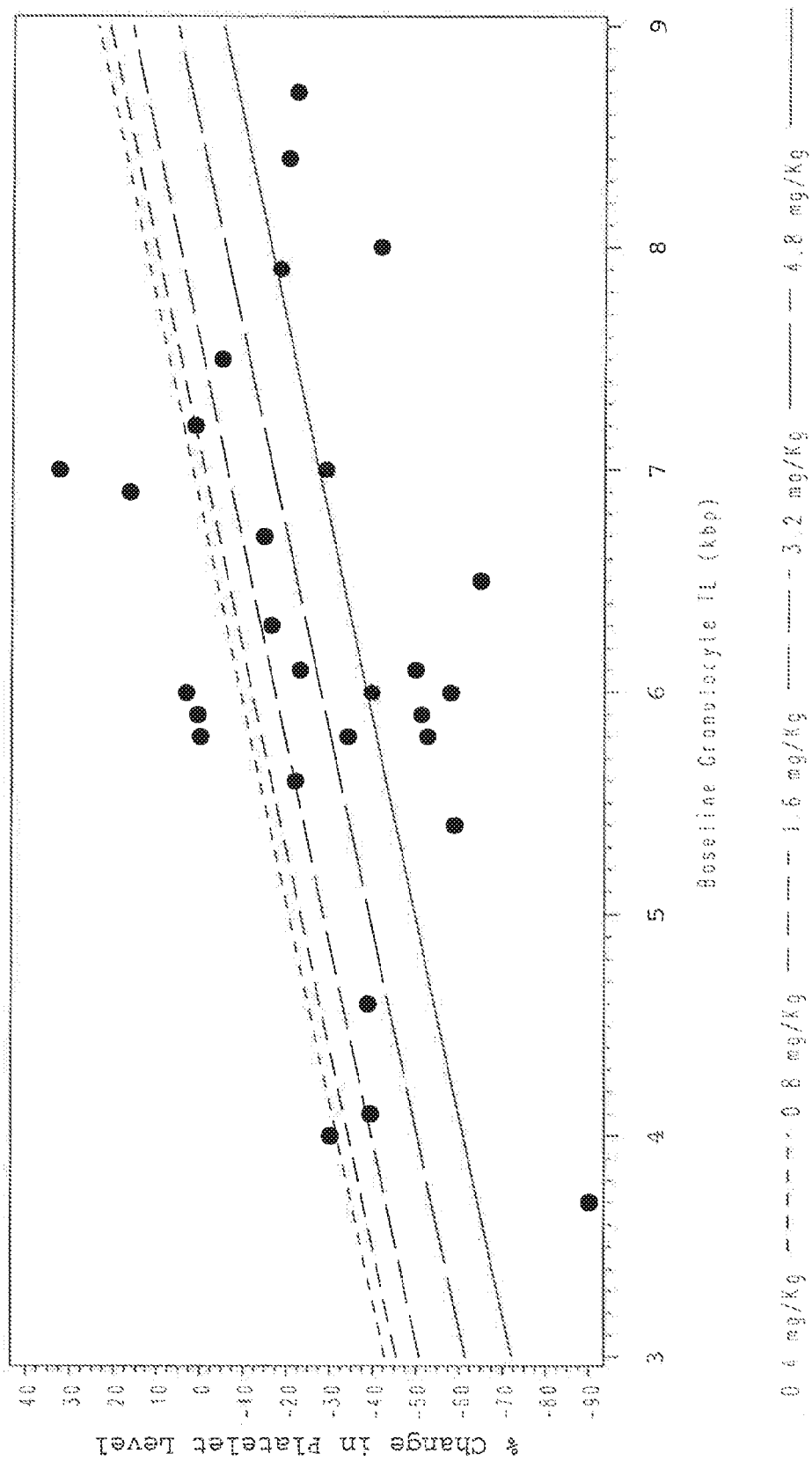
FIG. 5 is a graph showing the change in platelet levels at 5 week nadir versus the baseline granulocyte telomere length in the study patients. Circles indicate patients dosed with 0.4, 0.8 and 1.5 mg/kg. Triangles indicate patients dosed with 4.8 mg/kg.
Figure 6:
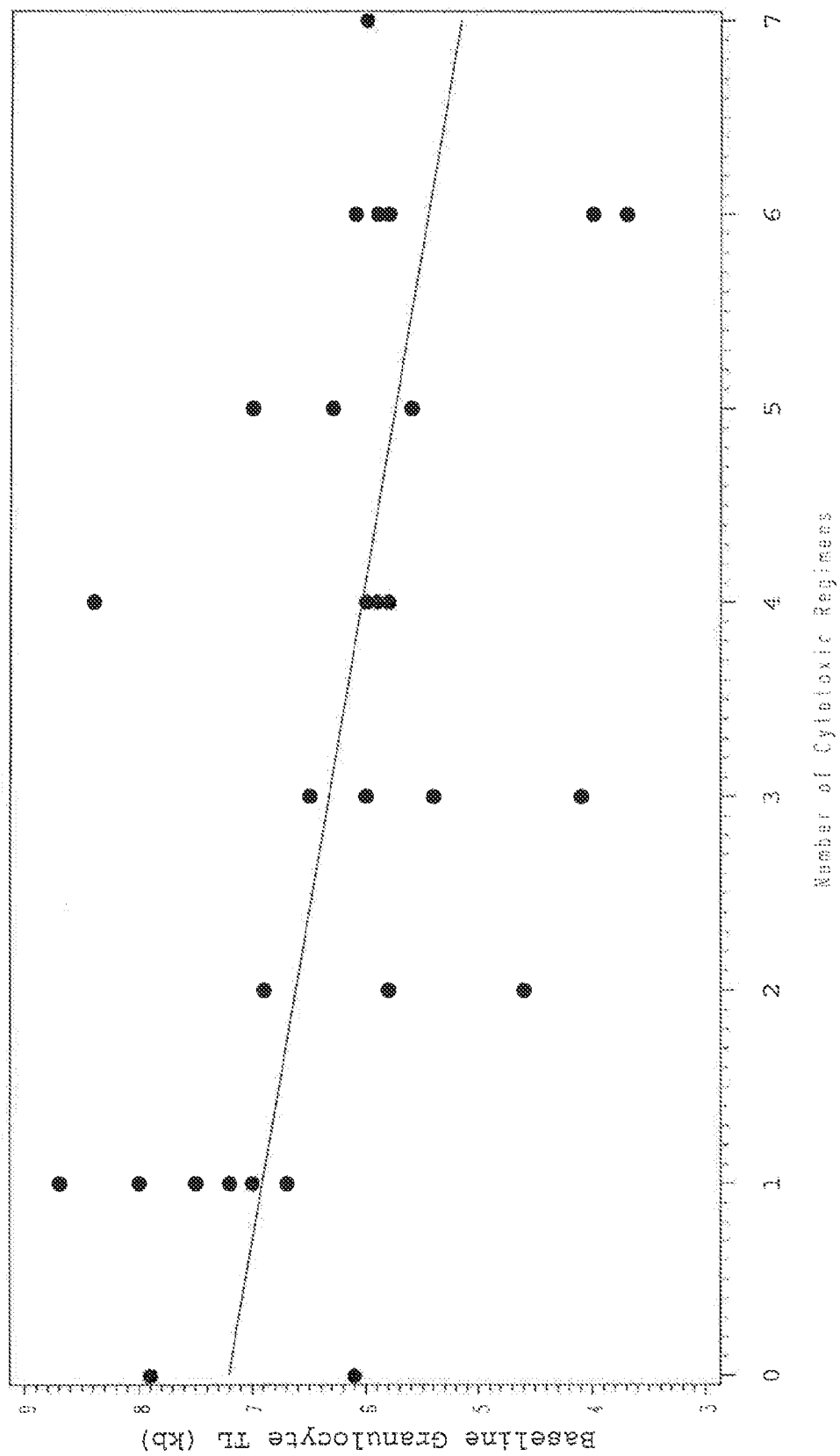
FIG. 6 is a graph showing the change in baseline granulocyte telomere length at 5 week nadir versus the number of cytotoxic regimens experienced by the patients prior to enrollment in this study.

The change in platelet levels after 4 weeks of treatment with GRN163L was plotted relative to the baseline median telomere length in each patient in FIG. 5.

The first model included 20/28 patients. Dose and baseline granulocyte telomere length were significant predictors. No dose by telomere length interaction was found.

TABLE 4

Multivariate Analysis

| Predictor | Regression Coefficient | P Value |
|---|---|---|
| Dose | −7 | 0.034 |
| Baseline Granulocyte Telomere length | 8 | 0.023 |

The model was extended to include 8 additional patients (all 28 patients in Cohorts 1-5). The relationships detected in the earlier model remained significant. Baseline GRN163L dose level and median baseline Granulocyte telomere length were both predictive of the % decrease of platelet levels during the first 4 weeks of treatment

TABLE 5

Multivariate Analysis

| Predictor | Regression Coefficient | P Value |
|---|---|---|
| Intercept | −73.8 | 0.004 |
| Dose | −6.6 | 0.033 |
| Baseline Granulocyte Telomere length | 11.2 | 0.005 |
| Model: R-squared = 0.319853 | | |

FIG. 5 shows the percent change from baseline to the 4-week nadir in platelet levels as a function of baseline granulocyte telomere length. The lines indicate the percentage change as a function of the dose level of GRN163L.

The equation to describe the predicted number of platelets in a patient during the first 4 weeks of treatment is as follows;

Predicted # of platelets=baseline platelets number−(baseline platelet number×% change in platelets/100).

% change in platelet #=(−73.8)−6.6×inhibitor dose (mg/kg)+11.2×average telomere length (kbp)

In the univariate analyses of predictors of percent change in platelet levels, only granulocyte telomere length was significant (p=0.024).

TABLE 6

Univariate Analysis

| Predictor | Regression coefficient | p Value |
|---|---|---|
| Intercept | −84.54302 | 0.0018 |
| Baseline granulocyte telomere length | 9.17580 | 0.0241 |

Another model was then developed to identify predictors of log nadir platelet levels during the first 4 weeks. This model resulted in a higher $R^2$ value indicating a better fit to the data.

TABLE 7

Multivariate Analysis

| Predictor | Regression Coefficient (b) | p Value |
|---|---|---|
| Intercept | −0.38 | 0.725 |
| Dose (mg/kg) | −0.13 | 0.017 |
| Baseline Granulocyte Telomere Length | 0.25 | 0.001 |
| Log of Baseline Platelets | 0.80 | <0.001 |
| Model: R-squared = 0.645071 | | |

The equation to describe the predicted number of platelets in a patient at nadir during the first 4 weeks of treatment is as follows:

Predicted # of platelets= $e^{[(-0.38)-0.13 \times inhibitor\ dose\ (mg/kg)+0.25 \times average\ telomere\ length\ (kbp)+0.80 \times log\ of\ baseline\ platelet\ number]}$ In the univariate analyses of predictors of log nadir platelet levels, granulocyte telomere length, alone, was significant (p=0.004).

TABLE 8

Univariate Analysis

| Predictor | Regression coefficient | p Value |
|---|---|---|
| Intercept | 3.42818 | <.0001 |
| Baseline granulocyte telomere length | 0.27189 | 0.0040 |

Prediction intervals may be calculated, for example, to predict likely percent change in platelet levels or the platelet nadir for patients or subjects with a particular set of baseline and treatment values, for example, telomere length, baseline platelets and dose level. The regression equation provides the expected value for a future individual with specified covariates (J. Neter et al. *Applied linear statistical models: regression, analysis of variance, and experimental designs*, 3$^{rd}$ edition pp. 81-83 (1990)). However, due to sampling distribution error as well as interindividual variability, a patient may have platelet levels that fall above or below that predicted value. A series of prediction intervals may be created with decreasing coverage. For example, a 99% prediction interval with upper and lower bounds $P_{U99}$ and $P_{L99}$ may be created and would, on average, contain 99% of the patients' observed platelet levels. A 90% prediction interval with upper and lower bounds $P_{U90}$ (<$P_{U99}$) and $P_{L90}$ (>$P_{L99}$) may be created and would, on average, contain 90% of future observed platelet levels. This allows one to determine the likelihood that the patient would develop a grade 3 or 4 thrombocytopenia.

The average telomere length of normal cells differs among individuals and declines with age as shown by the percentiles in FIG. 7. Granulocyte telomere lengths in the 28 patients in this study are generally shorter than normal, which is consistent with the effects of physiologic stress and chemotherapy. Although prior chemotherapy history as tabulated here was not predictive of platelet decreases, it was highly correlated with baseline telomere lengths in a univariate analysis. The telomere length measurement reflects prior treatment effects along with other hereditary or acquired influences with high precision. Age was also a significant predictor of telomere length.

The results from this study demonstrate a close correspondence between baseline telomere length values as determined by the described test and the risk of the patient developing dose limiting thrombocytopenia.

Although the invention has been described with respect to particular embodiments and applications, those skilled in the art will appreciate the range of applications and methods of the invention disclosed herein and the invention is not limited to such embodiments.

All references cited throughout the disclosure are hereby expressly incorporated by reference herein in their entireties.

The invention claimed is:

1. A method of telomerase inhibition therapy for a human subject in need thereof, the method comprising:
administering to a human subject in need of telomerase inhibition therapy and susceptible to an adverse reaction from telomerase inhibition therapy at least about 1.6 mg/kg to about 20 mg/kg of GRN163L to a human subject on day 1 and on approximately day 8 of a 21 day cycle to inhibit telomerase and the proliferation of cancer cells in the human subject with a reduced risk of an adverse reaction selected from thrombocytopenia, anemia, leucopenia and neutropenia.

2. A method of telomerase inhibition therapy for a human subject in need thereof, the method comprising:
administering to a human subject in need of telomerase inhibition therapy and susceptible to an adverse reaction from telomerase inhibition therapy at least about 1.6 mg/kg to about 20 mg/kg of GRN163L to a human subject on day 1 and on approximately day 15 of a 28 day cycle to inhibit telomerase and the proliferation of cancer cells in the human subject with a reduced risk of an adverse reaction selected from thrombocytopenia, anemia, leucopenia and neutropenia.

3. A method of telomerase inhibition therapy for a human subject in need thereof, the method comprising:
administering to a human subject in need of telomerase inhibition therapy and susceptible to an adverse reaction from telomerase inhibition therapy about 1.6 mg/kg to about 20 mg/kg of GRN 163L to a human subject two times in the first week in a 14 day cycle inhibit telomerase and the proliferation of cancer cells in the human subject with a reduced risk of an adverse reaction selected from thrombocytopenia, anemia, leucopenia and neutropenia.

4. The method of any one of claims 1-3, wherein the administering is of about 3.2 mg/kg to about 20 mg/kg to the subject.

5. The method of claim 4, wherein the administering is of about 4.8 mg/kg to about 20 mg/kg to the subject.

6. The method of claim 5, wherein the administering is of about 6.2 mg/kg to about 20 mg/kg to the subject.

7. The method of claim 6, wherein the administering is of about 7.2 mg/kg to about 20 mg/kg to the subject.

8. The method of claim 7, wherein the administering is of about 9 mg/kg to about 20 mg/kg to the subject.

9. The method of claim 8, wherein the administering is of about 12 mg/kg to about 20 mg/kg to the subject.

10. The method of claim 1, wherein the subject is being treated for a cancer selected from breast cancer, colon cancer, lung cancer, prostate cancer, testicular cancer, hepatocellular cancer, gastric cancer, gastrointestinal cancer, pharynx cancer, rectal cancer, pancreatic cancer, cervical cancer, ovarian cancer, liver cancer, bladder cancer, cancer of the urinary tract, thyroid cancer, renal cancer, skin cancer, brain cancer, carcinoma, melanoma, leukemia and lymphoma.

* * * * *